(12) United States Patent
Hunter et al.

(10) Patent No.: US 8,116,982 B2
(45) Date of Patent: Feb. 14, 2012

(54) SYSTEM AND METHOD FOR AUTOMATIC COLOR SEGMENTATION AND MINIMUM SIGNIFICANT RESPONSE FOR MEASUREMENT OF FRACTIONAL LOCALIZED INTENSITY OF CELLULAR COMPARTMENTS

(75) Inventors: Edward A. Hunter, San Diego, CA (US); Randall Scott Ingermanson, San Diego, CA (US); William Scott Callaway, San Diego, CA (US)

(73) Assignee: Vala Sciences, Inc., San Diego, CA (US)

( * ) Notice: Subject to any disclaimer, the term of this patent is extended or adjusted under 35 U.S.C. 154(b) by 1122 days.

(21) Appl. No.: 10/507,442

(22) PCT Filed: Mar. 13, 2003

(86) PCT No.: PCT/US03/07968
§ 371 (c)(1),
(2), (4) Date: Mar. 15, 2006

(87) PCT Pub. No.: WO03/078965
PCT Pub. Date: Sep. 25, 2003

(65) Prior Publication Data
US 2007/0016373 A1    Jan. 18, 2007

Related U.S. Application Data

(60) Provisional application No. 60/363,889, filed on Mar. 13, 2002.

(51) Int. Cl.
*G01N 33/50* (2006.01)

(52) U.S. Cl. .............. 702/19; 702/28; 702/32; 382/133; 382/164; 382/173

(58) Field of Classification Search .................. None
See application file for complete search history.

(56) References Cited

U.S. PATENT DOCUMENTS 5,528,703 A * 6/1996 Lee ................................. 382/257
6,416,959 B1 * 7/2002 Giuliano et al. ............... 435/7.2

OTHER PUBLICATIONS

Pohl et al. (Pharmaceutical research, vol. 16, No. 2, p. 327-332, 1999).*
Sudbo et al. (Analytical Cellular Pathology, 21, p. 71-86, 2000).*

* cited by examiner

*Primary Examiner* — Karlheinz R Skowronek
(74) *Attorney, Agent, or Firm* — INCAPLAW; Terrance A. Meador

(57) ABSTRACT

A system, a method, and a programmed device for measurement of translocational activity among cellular compartments process magnified images of cellular material exposed to an agent by segmenting and compartmentalizing the images and then measuring fractional localized intensity of two or more components in the segmented, compartmentalized image. The measured fractional localized intensities are compared to determine translocation of cellular material among the measured components caused by the agent.

4 Claims, 31 Drawing Sheets

FIGURE 21a
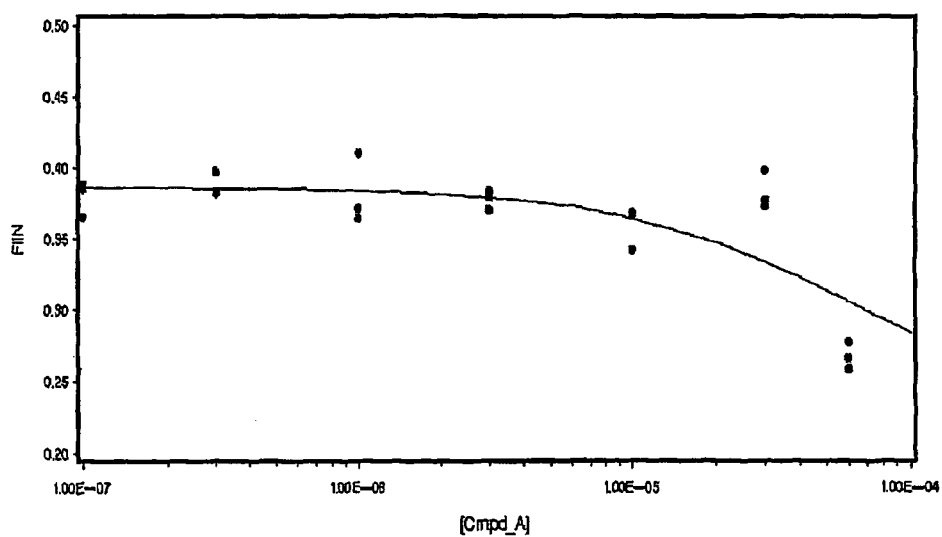
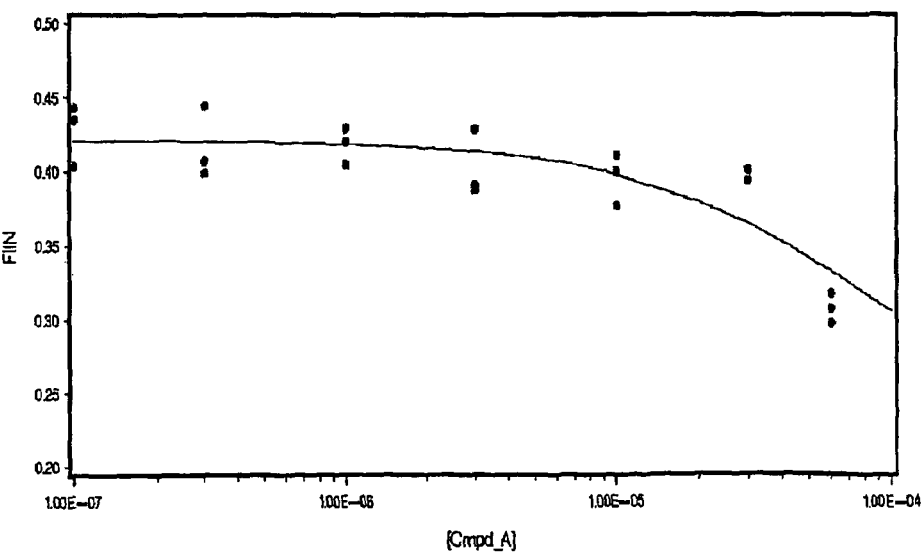
FIGURE 21b

FIGURE 22a
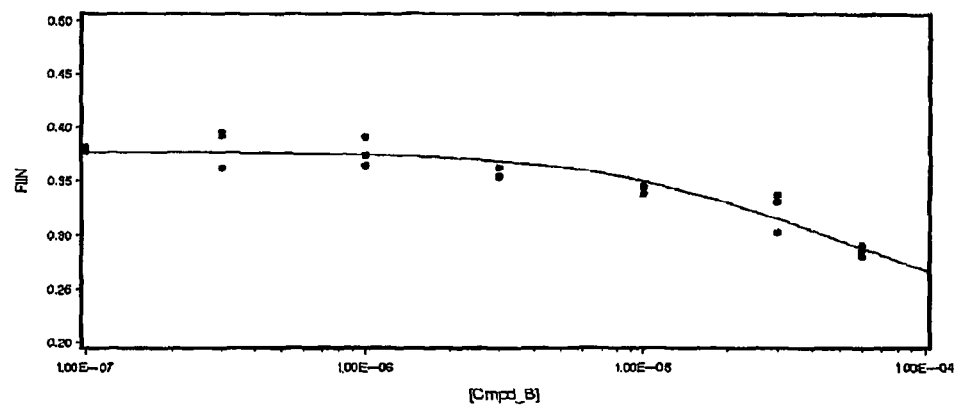
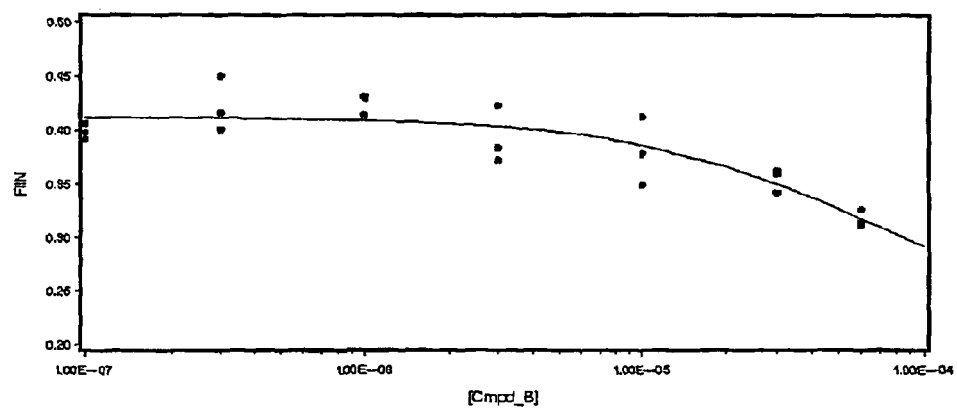
FIGURE 22b

FIGURE 23a
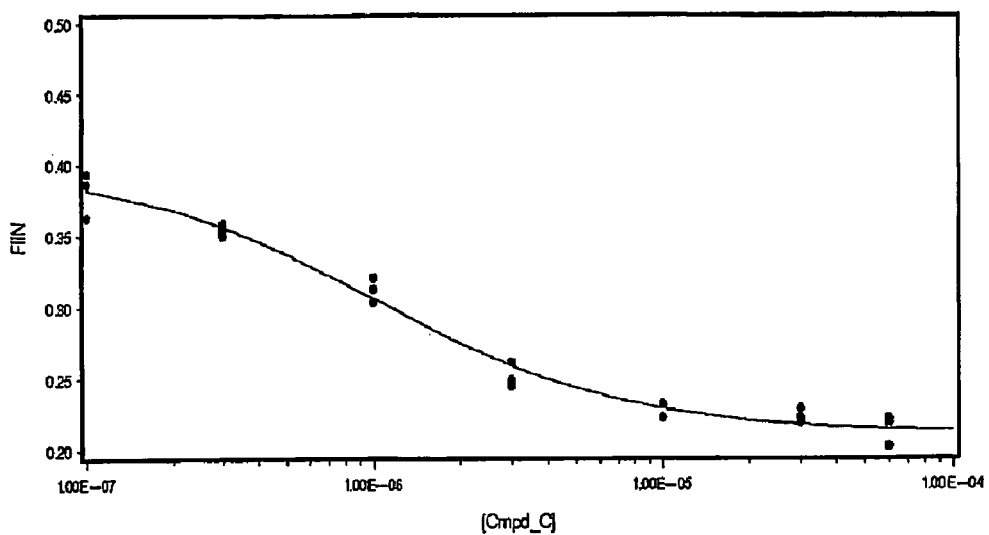
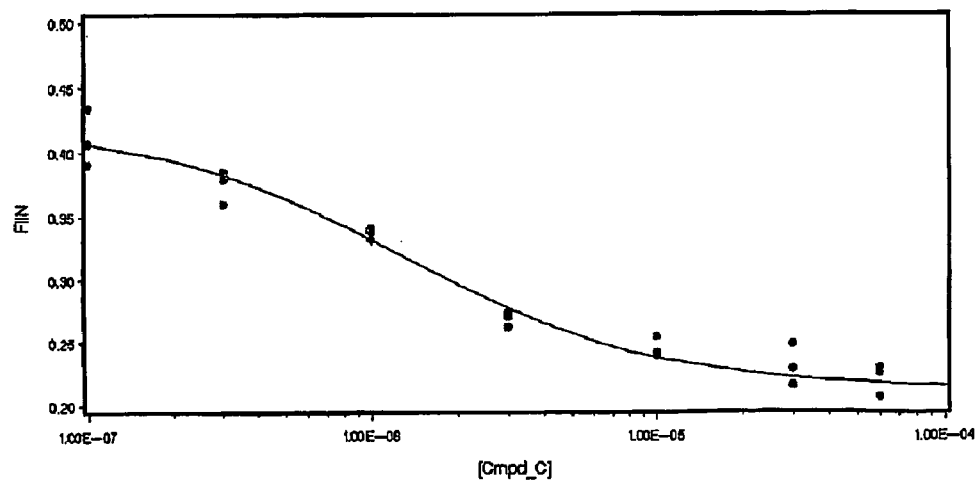
FIGURE 23b

| Super User/Manager Preset Parameters |  |
|---|---|
| Type I Error | 5.0 % |
| Type II Error | 5.0 % |

Figure 26a

| Assay Specific, Measured Values |  |
|---|---|
| Variability of FLIC (SD or CV) | 1.0 % |
| Amplitude FLIC (Max-Min Controls) | 18 % |

Notes
   Standard Deviation (SD)
   Coefficient of Variation (CV)
   CV = (SD/mean)x100
Either SD or CV can be entered

Figure 26b

Screening Parameters

| | |
|---|---|
| Time/Plate | 10 m |
| Cells/Image | 30 |
| Minimum Significant Response (MSR) | 10 % |
| Cells/Well Required for MSR | 57 |

Notes
Enter Time/Plate
    MSR and Cells/Well are
    auto calculated and displayed
    MSR is based on average cells/image
Enter MSR
    Estimated Time/Plate and Cells/Well are
    auto calculated and displayed
Enter Cells/Well
    Estimated Time/Plate and MSR are
    auto calculated and displayed based
    on average cells/image

Figure 27

SYSTEM AND METHOD FOR AUTOMATIC COLOR SEGMENTATION AND MINIMUM SIGNIFICANT RESPONSE FOR MEASUREMENT OF FRACTIONAL LOCALIZED INTENSITY OF CELLULAR COMPARTMENTS

RELATED APPLICATIONS

This application claims priority from U.S. Provisional Patent Application 60/363,889 filed Mar. 13, 2002.

TECHNICAL FIELD

This application concerns assay of biological material by means of high speed, high throughput cytometry using fractionalized localized intensities of subcellular components in magnified images.

BACKGROUND ART

Drug discovery screening has historically used simple well-based read-outs in order to handle a high throughput of lead compounds. However, a given assay currently provides only the information that a drug affects some of the cellular processes that result in the response measured; the exact nature of the target for the drug is not indicated. A cell-based assay is a model system designed to identify compounds that interact with a selected molecular target in a specific manner. Cell-based assays are robust in that they approximate physiological conditions, and they can yield highly complex information. This requires sophisticated image analysis tools and streamlined data handling. Multi-parameter cell assays, where a response is measured by multiplexed reporter molecules, as well as morphological criteria, have been limited by the labor-intensive nature of imaging and analyzing subcellular details. The power of obtaining more complex information earlier in the screening process demands effective solutions to this bottleneck.

Dissecting the steps in cellular pathways is important, because multiple pathways converge and diverge to provide redundancy (backup in case of cellular dysregulation) and as a coordinated response. Whereas a given drug may result in, e.g., the secretion of a cytokine (such as Interleukin 2 (IL-2) measured as a single parameter response in a well plate) the researcher does not know which signaling pathway was utilized, or what other cellular responses were initiated. If the signaling pathway used also led to cell death, the efficacy of the candidate drug would be compromised and would fail in costly and controversial animal testing. Multiplexed cellular responses need to be investigated to eliminate this kind of false positive lead in drug discovery.

The complexity of real cell responses also leads to heterogeneity between cells, even in a cloned cell line, depending on other factors such as cell cycle progression. Thus, a lead which acts on a cellular process which is part of DNA synthesis would elicit a response only in those cells which were in S phase at the time the drug was added. In the clinical situation, continuous infusion can ensure all cells are treated, and so the lead is a viable candidate. If an average response from all the cells in a well is measured, it may fall below the threshold for detection and result in a false negative: an effective drug is overlooked.

Pharmaceutical companies continually demand faster analysis of screening tests. Automation has addressed the need to increase data acquisition, but there remain stringent requirements for accuracy, specificity and sensitivity. Preliminary data indicates that the higher the information content of the assay read-out, the less variability there is between individual cells in a responding population Thus, the total number of cells needed to attain the confidence level required by the experiment is decreased, resulting in increased throughput. More accurate analysis results in better dose response information. Higher quality data results in better data mining and identification of drugs with significant clinical impact.

Automated quantitative analysis of multiplexed fluorescent reporters in a population of intact cells at subcellular resolution is known. Accurate fluorescence quantification is made possible by technological advances owned by Q3DM, the assignee of this application, and the rapid processing of this complex image data in turn depends on unique computational processes developed by Q3DM. High throughput microscopy has only recently become possible with new technological advances in autofocus, lamp stabilization, image segmentation and data management (e.g., U.S. Pat. Nos. 5,548,661, 5,790,692, 5,790,710, 5,856,665, 5,932,872, 5,995,143, and U.S. patent applications Ser. Nos. 09/703,455 and 09/766,390). Accurate, high-speed autofocus has enabled fully automated "walk-away" scanning of arbitrarily large scan areas. Quantification is dramatically improved by controlling the intensity of illumination, and is dependent on accurate autofocus. Advances in image segmentation make detection of both dimly and brightly stained cells simple, so that heterogeneous cell populations can be assayed with statistically meaningful results. Finally, rapid streaming of high information content data depends on efficient image data format and caching. Together, these technological advances enable retrieval of high quality, image-based experimental results from multiplexed cell based assays.

SUMMARY AND ADVANTAGES OF THE INVENTION

The most comprehensive tool set that biology drug discovery could possess at this time would be one that could integrate technologies involving the acquisition of molecular, cell-structural, and cell-activity data. Application of such a tool set to Biology programs would transform current end-point cell-assays from indirect read-outs (such as IL2) to sub-cellular structural co-localization analyses, and time-lapse imaging of cell function activities. Quantitative cell imaging technologies will lead the way to the next level of rational drug screening and design.

With the automation of this rate-limiting step in the discovery pipeline comes the possibility of designing high throughput cell-based assays that occur in the context of the whole cell, as well as the ability to multiplex reporter molecules so that complex cellular interactions may be taken into account. These assays would have measurable economic advantages, because in obtaining more data earlier, they offer the possibility of eliminating false positives and false negatives due to heterogeneity in cellular response. The benefit to drug discovery is that lead compounds are better qualified before they enter costly and controversial animal trials.

These improvements and advantages are provided by this invention which is realized as an assay system and method for automating color segmentation and minimum significant response in measurement of fractional localized intensity of cellular compartments.

Assay development may yield unexpected results, therefore the invention provides the ability to visually inspect cells identified on a multi-parametric data plot Gating the cells of interest generates an immediate montage on a display screen, and by relocation of the scanning stage, the user can look through a microscope eyepiece for validation.

New assay development demands that the assay system be adaptable to novel reporter molecules, to new cell types, and to the visual nature of the cellular response. To this end, the assay system of the invention uses object-oriented software framework to be open and extensible so that features such as hardware, measurement or database functions, and cell classification schemes can be added without having to uncover large portions of existing software. In particular, adaptive object recognition algorithms incorporated into the assay system of the invention, including image segmentation and tessellation, allow a user to interactively define what constitutes an object of interest in an assay (i.e. the nucleus of a given cell type). Implemented interactively, these algorithms are incorporated into scanning parameters for that assay, so that automated image segmentation and tessellation can enable the speeds necessary for high throughput screening.

The accuracy of fluorescence measurements is enhanced due to high performance features, notably autofocus, lamp stabilization, image segmentation, image tessellation, and image measurement algorithms. The resulting increase in the signal-to-noise ratio of the data is evident-in diminished residuals in a best-fit curve, providing enhanced sensitivity.

BRIEF DESCRIPTION OF DRAWINGS

FIGS. 21a and 21b illustrate inhibition of NFκB nuclear translocation by BIPI compound A.

FIGS. 22a and 22b illustrate inhibition of NFκB nuclear translocation by BIPI compound B.

FIGS. 23a and 23b illustrate inhibition of NFκB nuclear translocation by BIPI compound C.

FIGS. 26a and 26b are illustrations of first and second graphical user interface (GUI) tools used to initialize a drug screen according to the invention.

FIG. 27 is an illustration of a third GUI tool used to initialize a drug screen according to this invention.

DETAILED DESCRIPTION

Figure 1:
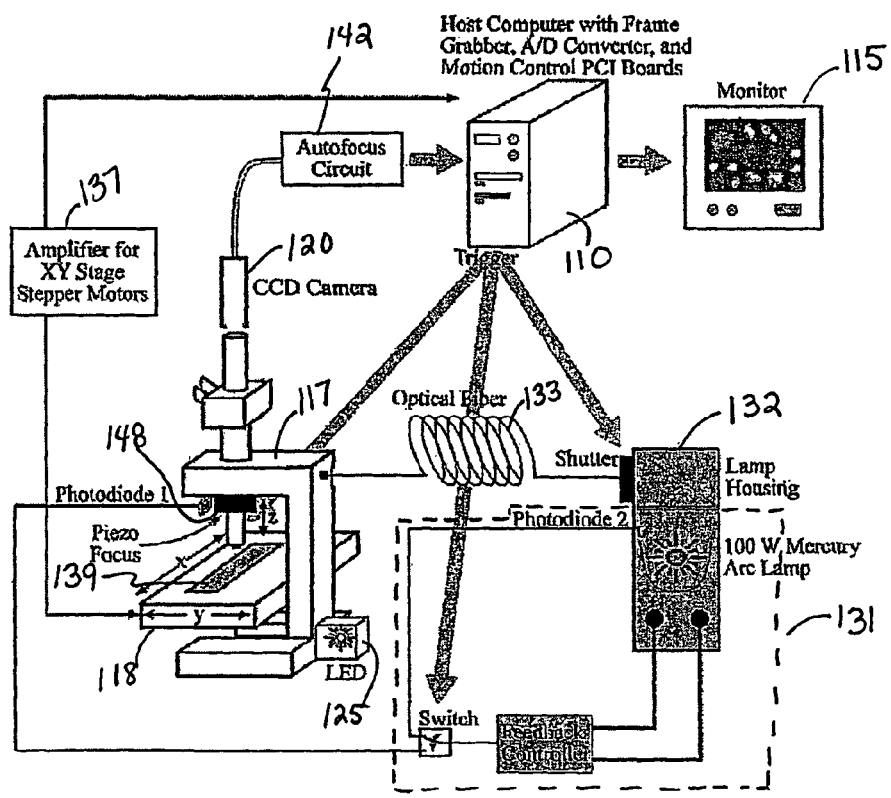
FIG. 1 is a block diagram of an automated microscopy system according to this invention.

Fractional Localized Intensity of Cellular Compartments (FLIC)

Development of multicompartment models for cellular translocation events: Many potentially important molecular targets are regulated not only in their expression levels, but also by their subcellular or spatial localization. In the post-genomics era, illuminating the function of genes is rapidly generating new data and overthrowing old dogma The prevailing picture of the cell is no longer a suspension of proteins, lipids and ions floating around inside a membrane bag, but to involves protein complexes attached to architectural scaffolds or chromatin provided by the cytoskeleton, endoplasmic reticulum, Golgi apparatus, ion channels and membrane pores. Cell surface receptors are oriented within the plasma membrane such that they can bind an extracellular molecule and initiate a response in the cytoplasm. Protein complexes in the cytoplasm can be dissociated following regulated proteolysis to release specific DNA binding proteins. These proteins then pass through nuclear pores, interact with the chromatin organization, and regulate gene transcription. Proteins are then trafficked through the Golgi apparatus where they are readied for functionality. Any of these processes can be targets for improving clinical efficacy and reducing side effects, and as such are important to understand.

A typical assay to screen for an agonist or antagonist for this process would measure the movement of a known DNA binding protein from the complex into the nucleus. However, by multiplexing reporter molecules, the same assay can also provide information on the receptor internalization. Thus the user can be sure of which receptor is responding to the drug when the downstream effect is mediated. Broadly speaking, there is a need to visualize protein movement as a response to the activation of target signaling molecules, specifically receptors on the external membrane binding their ligand (or drug) and internalizing, as well as transcription factors moving from cytoplasm to nucleus. The definition of discrete compartments has been achieved by compartment specific labeling (dyes). The plasma membrane is labeled with a lipophilic carbocyanine dye, the cytoplasm with a dye that permeates live cells but is cleaved in the cytoplasm so that it cannot diffuse out and the nucleus by a membrane-permeant DNA intercalating agent Round cells such as lymphocytes present a challenge in identifying nuclear, cytoplasmic, and membrane compartments. Resolving the sparse cytoplasmic compartment requires high resolution imaging, achieved using a high numerical aperture objective lens, but this also narrows the depth of field. There are many subcellular components, organelles or patterns that also require high-resolution images. Robust autofocus becomes necessary; this must be done rapidly to meet the demands of high throughput screening, and to ensure accurate quantification of fluorescence intensity. The invention employs an autofocus mechanism that is an order of magnitude faster than other systems available because it uses a dedicated circuit to measure image sharpness directly from the video signal. Such an autofocus mechanism is robust because it measures the change in the optical transfer function (OTF) in a range that avoids the contrast reversals inherent in cell images.

The assays used for generating preliminary data will may include a second reporter molecule that detects a separate protein. Desirably, more parameters may be measured in the same cell over a given time period. By the use of an object-oriented software framework, the platform employed by this invention is extensible and algorithm-driven for maximum flexibility. To give a hypothetical case, a simple comparison of two spatial patterns (e.g., nuclear and cytoplasmic fluorescence) may be insufficient to determine the efficacy of a lead on a target. Even though the positive response occurs, if this is accompanied by changes in cell morphology or metabolism, the efficacy may be questionable, or toxicity may be a more important limitation. The addition of reporters for these cell properties will require additional image analysis algorithms that will classify a set of cellular responses. Preferably the invention utilizes software plugin architecture in order to meet these needs by supporting development of new, assay specific processing modules into the image analysis capabilities of the base platform and existing assays.

A high throughput microscopy platform utilized in the practice of the invention is illustrated in FIG. 1. This platform includes a high performance, research-grade instrument built as an attachment system around a commercial fluorescence microscope. The platform includes a programmable digital (host) computer 110, preferably a high-end, off-the-shelf PENTIUM® workstation running the WINDOWS® operating system. Developed and validated assays may be run on this system using a straightforward, point and click operation based upon familiar WINDOWS® operating system motifs. Other components of this platform include a live monitor 115, an inverted NIKON® TE300 fluorescence microscope 117 with attachments that include a robotic stage 118, a CCD (charge coupled device) camera 120, and an LED phase contrast light source 125. A stabilized mercury arc lamp mechanism 131 provides illumination for operation of the microscope by way of fiber optic housing 132 and an optical fiber 133. A control unit 137 drives the stage 118 while it supports a structure 139 (such as a microtiter plate or another equivalent assay device) disposed on the stage 118 in response to commands issued by the host computer 110 and host computer. An autofocus circuit 142 responds to images of obtained by the CCD camera 120, providing processed information to the host computer 110. A piezofocus mechanism 148 controls the positioning of the lens mechanism of the microscope 117 in order obtain a best focus. The host computer 110 is programmed to perform routines for focusing the microscope 117, controlling the stabilized mercury arc lamp mechanism 131, scanning the structure 139 by moving the stage 118, intaking and storing sequences of magnified images of biological material on the structure 139 produced by the CCD 120, processing the magnified images by segmentation and tessellation, and performing the translocation processing described in more detail below.

Figure 2:
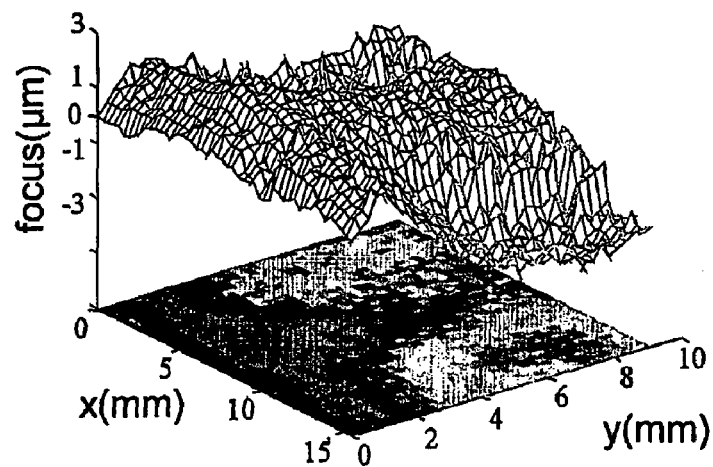
FIG. 2 is a plot showing a surface of best foci in a 9×15 square millimeter area.

Autofocus is critical for scanning large areas due to the variations in slide and coverslip surfaces and mechanical focus instability of the microscope (particularly thermal expansion) [M Bravo-Zanoguera and J H Price. Analog autofocus circuit design for scanning microscopy. In *Proceedings, International Society for Optical Engineering (SPIE), Optical Diagnostics of Biological Fluids and Advanced Techniques in Analytical Cytology*, volume 2982, pages 468-475, 1997]. These effects combine to effectively create an uneven surface over which the cells must be analyzed. An example of this uneven surface is plotted in FIG. 2, a 3D plot of a surface of best foci (9×15 mm$^2$ area) demonstrating the need for autofocus. The plot represents the surface of best foci with the average plane subtracted and shows a range of 6 µm. [M Bravo-Zanoguera, B von Massenbach, A Kellner, and J H Price. High performance autofocus circuit for biological microscopy. *Review of Scientific Instruments*, 69(11):3966-3977, 1998]. As can be appreciated with reference to this figure, the foci can easily vary through a range of ±10 µm over an entire microscope slide. This can have a dramatic effect on the ability to locate cells. Using a NIKON® Fluor 0.75 NA 20× objective, for example, the mean fluorescence intensity has been shown to drop by about 35% at ±10 µm from focus [J H Price and D A Gough. Comparison of digital autofocus functions for phase-contrast and fluorescence scanning microscopy. *Cytometry*, 16(4):283-297, August 1994].

Figure 3:
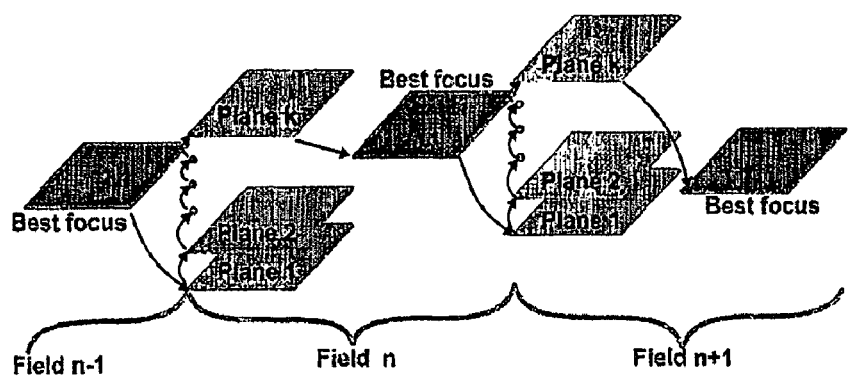
FIG. 3 is a diagram demonstrating a process using incremental scanning to obtain a best focus which may be used in the practice of this invention.

FIG. 3 is diagram demonstrating incremental scanning. Best focus from the previous field provides the center of the autofocus search range for the next field. The degree of focus (sharpness) is then measured for several test planes (typically 5-9) at the video interlaced field rate of 60 Hz, and the piezo-electric positioner is moved to best focus. Stage movement and autofocus require a total of 0.3 s.

Incremental scanning is carried out by moving the stage to a field, stopping the stage, performing autofocus, acquiring the image and repeating on the next field. This sequence is shown in FIG. 3. If focus lies too close to one extreme of the search range, the center of the range can be repositioned and autofocus repeated.

Autofocus on single fields has been extensively explored and reviewed [Price & Gough]. Further work has extended the techniques to large numbers of microscope fields and performing high-speed autofocus with real time image processing [Price & Gough]. Careful attention to magnification and sampling led to about 100 nm precision (as measured by the standard deviation) in scans of thousands of microscope fields with focus achieved in 0.25 s. Further development of this technology led to design and implementation of an autofocus circuit that tremendously reduced the cost of autofocus and improved focus precision to an average of 56 nm [Bravo-Zanoguera et al.]. Additional theoretical and experimental studies on the through-focus OTF helped further support the choice of the correct filter for use in isolating the high frequencies for focus measurement [M A Oliva, M Bravo-Zanoguera, and J H Price. Filtering out contrast reversals for microscopy autofocus. *Applied Optics,* 38(4):638-646, February 1999].

range is 6.2-16.9 µm and is largest for the biggest area. The nonplanar range is 1.6-4.1 µm and is still much larger than the depth of field of high NA objectives. Other experiments (data not shown) indicated that the absolute variation from flat increases with area as expected. For example, data from larger

TABLE 1

Autofocus performance in scanning

| | Experimental Conditions | | | | | Best Focus Range | | Combined σ | | Mean Digital-Analog |
|---|---|---|---|---|---|---|---|---|---|---|
| | Area | | | Test Range | | Max–min(µm) | | Digital | Analog | |
| Experiment | (mm × mm) | Fields | Z(µm) | Positions[a] | Zoom | Raw | Nonplanar[b] | (µm) | (µm) | (µm) |
| 1[c,d] | 3.25 × 1.91 | 1200 | 1.465 | 11 | 2.0 | 6.2 | 2.8 | 0.146 | 0.106 | 0.144 |
| 2[d,e] | 3.48 × 2.05 | 1728 | 2.197 | 11 | 2.25 | 7.3 | 2.4 | 0.144 | 0.052 | 0.088 |
| 3[d,e] | 2.60 × 2.05 | 1296 | 2.196 | 11 | 1.1 | 7.9 | 1.5 | 0.036 | 0.027 | 0.043 |
| 4[d,e] | 3.63 × 2.84 | 2500 | 2.196 | 11 | 1.1 | 16.9 | 4.1 | 0.075 | 0.067 | 0.006 |
| 5[e,g] | 3.87 × 3.04 | 1296 | 2.296 | 11 | 1.5 | 10.5 | 2.1 | 0.031 | 0.027 | 0.074 |
| 6[h,g] | 4.00 × 3.12 | 1369 | 2.196 | 11 | 1.5 | 12.8 | 1.6 | 0.028 | 0.023 | 0.068 |
| 7[h,i] | 3.87 × 3.04 | 1296 | 2.196 | 9 | 1.5 | 11.3 | 2.9 | 0.051 | 0.042 | 0.122 |

Figure 4:
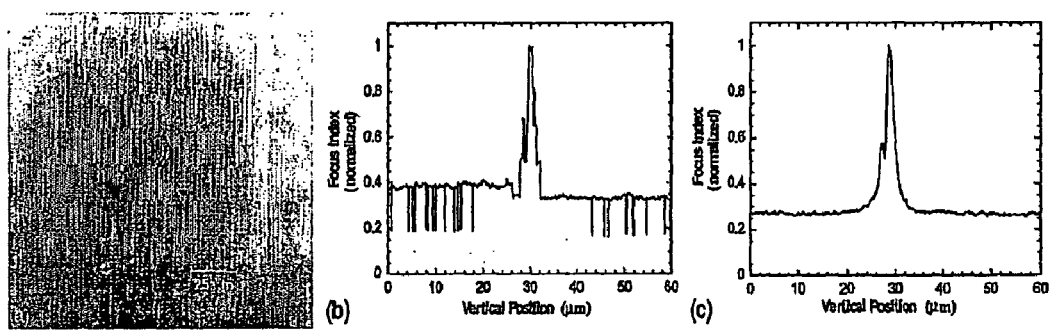
FIG. 4 illustrates autofocus circuit dynamic range and sensitivity.

[a]Focus time is (positions + 2)/60 s, or 0.18 s and 0.22 s for 9 and 11 test positions respectively
[b]Plane fit to data by linear regression and subtracted
[c]Linear spacing between focus planes
[d]Digital Tracking
[e]Nonlinear spacing between focus planes of 17, 10, 7, 6, 6, 6, 6, 7, 10 and 17 digital units
[f]48% overlap between contiguous fields
[g]Analog tracking
[h]Tracked by average of analog and digital
[i]Nonlinear spacing between focus planes of 22, 10, 7, 6, 6, 7, 10 and 22 digital units FIG. 4 includes three panels that illustrate autofocus circuit dynamic range and sensitivity demonstrated using (left) a microscope field with no cells and only a small amount of debris. (Center) shows the plot with autogain disabled (gain of 1.0), and (right) shows the plot with an autogain of 100.

Figure 5:
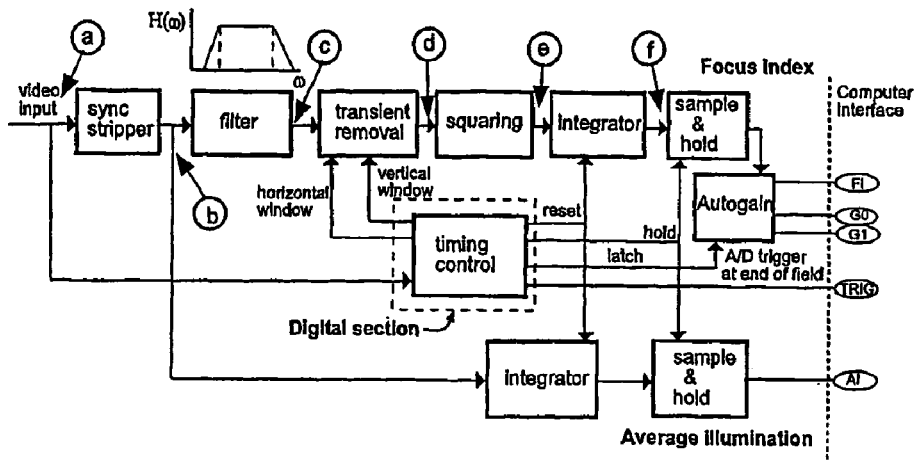
FIG. 5 is a block diagram of an autofocus measurement circuit which may be used in the practice of this invention.

The autofocus circuit illustrated in FIG. 5 was tested under typical scanning conditions [M Bravo-Zanoguera, B von Massenbach, A Kellner, and J H Price. High performance autofocus circuit for biological microscopy. *Review of Scientific Instruments,* 69(11):3966-3977, 1998.]. The purpose of the scanning experiments was to determine the ability of the system to track focus, as well as measure precision and compare the analog circuit to the digital system. Seven rectangular areas, ranging from 1200 to 2500 fields, were scanned in a raster pattern. The results are shown in Table 1. For the first six experiments, focus was computed from the power-weighted average of the focus measurements from 11 different vertical positions. In the final experiment, this number was reduced to 9 vertical positions. Autofocus was performed 20 times at each microscope field. The combined standard deviation (σ) of all autofocus trials (20 fields) in each experiment is shown in Table 1. For every experiment, the precision (as measured by σ) was better for the analog circuit than the digital system. The combined σ s for all seven experiments were 0.056 µm (analog) and 0.087 µm (digital). This is almost an order of magnitude better than the 0.528 µm depth of field (according to the Françon criterion [M Françon, editor. *Progress in Microscopy.* Row and Peterson, Evanston, Ill., 1961]) and approaches the minimum vertical step of 0.024 µm (PIFOC® piezoelectric objective positioner, Polytec PI, Irvine, Calif.).

Table 1 also includes two columns showing the range of best foci for each area scanned. In one column the raw data range is presented, while in the next column the range with the average plane subtracted is shown (nonplanar). The raw data $10\times 15$ mm$^2$ scans revealed a 6 µm range, and further experience scanning larger areas has led us to expect as much as a ±10 µm range of foci over an entire slide. This range is even larger (as much as hundreds of microns) for the wellplate formats that dominate many industrial microscopy applications.

The autofocus circuit of FIG. 5 provides very high sensitivity. However, it became clear early in the design process that the analog sensitivity was much greater than available with subsequent 12 bit A/D conversion. Thus, an autogain circuit was added to augment the dynamic range. FIG. 4 demonstrates the advantage of autogain, and the dynamic range and sensitivity of the circuit on a microscope field containing only small debris. We have found that this circuit is so sensitive that it can track focus even when no cells are present as long as there is something, even if only minimal debris, in the field.

Figure 6:
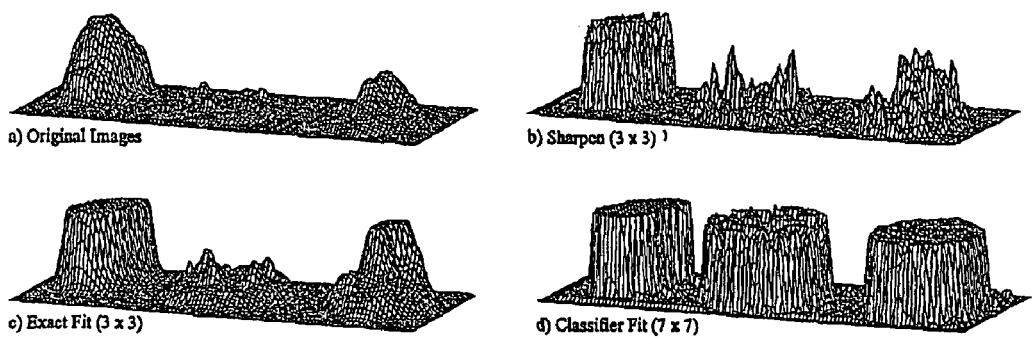
FIGS. 6a-6d, illustrate enhancement of contrast in magnified images by nonlinearly trained (perceptron criterion) 2D image filters.

It would be convenient if simple intensity thresholding were be adequate for quantitative cell-based assay of cells stained with relatively bright fluorescent dyes. Unfortunately, fluorescently stained cells invariably exhibit wide variations in stain because the cell size and fluorochrome densities vary. Accordingly, real-time image segmentation is utilized in this invention for fluorescently stained cell compartments in order to make subcellular compartment identification and localization much less dependent on fluorescence intensity or variability [J H Price, E A Hunter, and D A Gough. Accuracy of least squares designed spatial FIR filters for segmentation of images of fluorescence stained cell nuclei. *Cytometry,* 25(4) 303-316, 1996]. This work is illustrated in FIGS. 6a-6d, wherein enhancement by nonlinearly trained (perceptron criterion) 2D image filters to optimally approximate human texture classification capabilities is illustrated. In FIG. 6a, original images of three DAPI stained 3T3 cell nuclei are shown. FIG. 6b illustrates the result obtained with application of conventional image filters which do not provide adequate contrast enhancement. In FIG. 6c, linearly designed 2D filters also do not provide adequate contrast enhancement FIG. 6d illustrates that results obtained with nonlinearly designed filters provide dramatic contrast enhancement enabling simple intensity thresholding for a final segmentation step. This method utilizes nonlinear least-squares optimized image filters to create marked object-background contrast for automatic histogram-based thresholding. This contrast makes the final image segmentation much more threshold-independent, and allows dim cells to be segmented with the same accuracy as bright ones over a much larger intensity range than was previously possible. According to this method, the error function for filter design is allowed to sum only the error from a predetermined minimum contrast Allowing intensities to extend beyond this range, rather than requiring an exact match, substantially improved performance (see FIGS. 6a-6d). This method has been tested extensively over many years. For example, Price, Hunter and Gough tested ten montage images containing a combined 1,070 fluorescently stained cell nuclei. Each image was manually segmented to provide a standard. Then 3×3 through 25×25 element 2D filters were trained using the perceptron criterion and nonlinear least squares to optimally approximate the human standard. Each filter was tested against the other 9 images in order to ensure that the image did not bias this supervised design technique. Very high segmentation accuracy was achieved using this method, and there was little or no dependence of accuracy on the design image. In addition, the improvement in accuracy began flattening at the 7×7 filter size and did not improve beyond the 15×15 filter size. General purpose CPUs have advanced in processing power so that it is now possible to implement online image processing using 7×7 filters without any additional hardware. The fact that large filters are not required is advantageous for real-time operation.

This image segmentation mechanism provides the basis of fully automated, real-time cytometry from the in-focus image stream. The advantages of the precision and accuracy of this method result in improved measurement fidelity, improving system throughput and resolution as explored below.

Segmentation of objects from background using least-squares-designed contrast-enhancing filters can be used to find any cellular compartment or set of compartments from a set of fluorescence images. Tessellation can then be used to assign each cellular compartment to a cell. Image segmentation of the cell nuclei creates a single object for each cell. The nuclear masks are then fed to the tessellation algorithm to map out regions belonging to each cell and the remaining compartments are assigned to a cell based on those regions. Thus, tessellation provides an objective means to assign cellular compartments to cells.

Image segmentation of objects from background also does not separate overlapping objects. Even in carefully controlled cell cultures, cells may overlap. In many cytometry applications, measurements can be improved by cutting the overlapping objects apart Tessellation can be used to separate overlapping objects. Once the images of the cell nuclei have been segmented using contrast enhancing filters, the nuclear positions (e.g., centroids) can be input to the tessellation algorithm to cut the images of other overlapping cellular compartments apart and improve measurement fidelity. Mathematical morphology techniques (erosion and dilation) and the watershed algorithm are also often used to separate overlapping objects. For example, a cell membrane stain (e.g., DiI or DiD, Molecular Probes, Eugene Oreg.) or an amine whole cell stain (Alexa 488, Molecular Probes, Eugene Oreg.) can be used to identify the cytoplasmic and nuclear compartments together (the cytoplasmic compartment can be determined by subtracting the nuclear compartment). Erosion/dilation or watershed can then be used to separate the overlapping cells. Other cellular compartments (e.g., endoplasmic reticulum, ER) or vesicles can then be assigned to the cells based on the resulting image segmentation masks. However, very thin cellular regions of the cell that are very dim may not be segmented and may be absent from the resulting masks. Cell compartments such as ER or vesicles that fall on the missing areas will not be assigned to a cell. Tessellation can then be used to complete the assignment It also may be inconvenient or very difficult to add a stain to identify the cytoplasm. In the absence of a cellular mask, tessellation can be used to assign cellular compartments to cells (nuclear masks).

In this invention, once the magnified images of the cell nuclei have been segmented using contrast enhancing filters, tessellation of the segmented image is utilized to precisely define nuclear positions (e.g., centroids) in order to cut the images of other overlapping cellular compartments apart and improve performance. Tessellation, according to the unabridged, on line Merriam-Webster Dictionary is "a covering of an infinite geometric plane without gaps or overlaps by congruent plane figures of one type or a few types".

Figure 7:
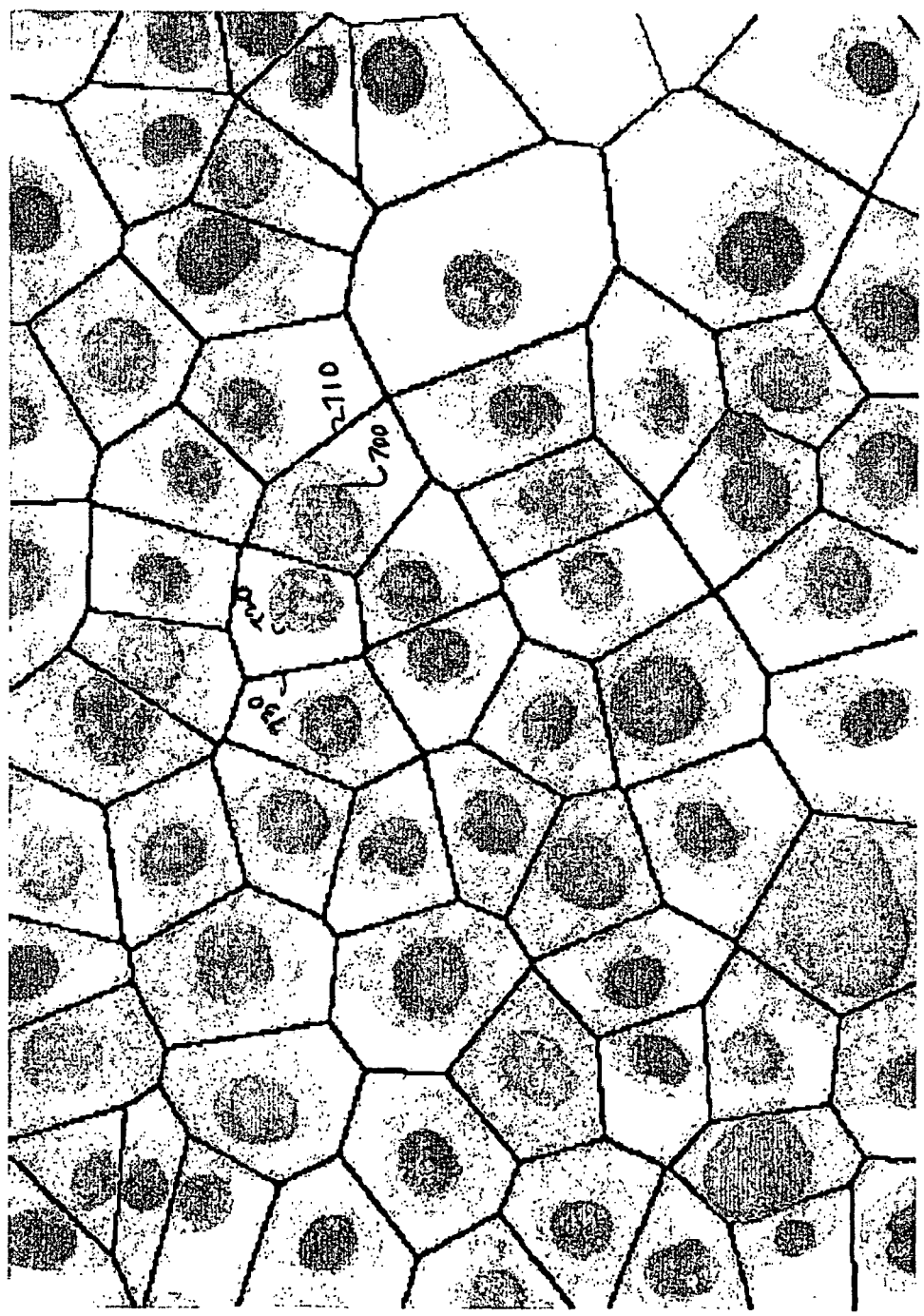
FIG. 7 is a magnified image of biological material showing tessellation of cell nuclei.

Essentially, tessellation of a magnified image in this description concerns the formation of a mosaic or a mesh of plane figures on a magnified image of cells in which each plane figure of the mosaic or mesh contains one object or compartment within a cell. Such objects or compartments include, without limitation, nuclei, membranes, endoplasmic reticuli, Golgi, mitochondria, and other cellular regions having protein concentrations that are organized in some way. Further, such magnified images are processed by segmentation to distinguish identical cell components, such as nuclei, from the background and all other cell components. The processed, segmented image is then tessellated to separate each of the distinguished cell components from nearby and overlapping neighbors. For is example, refer to FIG. 7 in which segmented cell nuclei are separated by a tessellation mesh of plane figures wherein each plane figure in the contains one nucleus. In this figure, for example, segmented nucleus 700 contained within the polygon 710 is separated and therefore distinguishable from its near neighbor nucleus 720 which is contained within polygon 730. Knowing the location, shape, and dimensions of each plane figure in the mosaic, the nuclei in the magnified image can be quickly accessed by traversing the mosaic in a regular fashion. The mesh in FIG. 7 is visible only in order to support an understanding of tessellation. In practice, the mesh resulting from tessellation can be visualized using conventional image processing, manual entry and display means. In processing of magnified images by programmed means, the mesh would, of course, also exist as one or more stored data structures. These data structures enable automation of tessellation by programming of the host computer 110.

Figure 8:
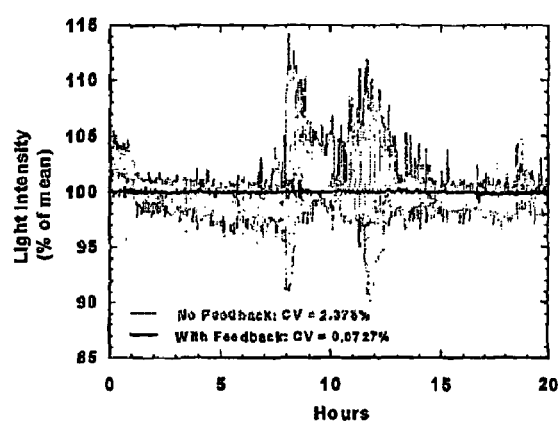
FIG. 8 is a plot showing results obtained using optical feedback stabilization of a 100 W Hg vapor arc lamp.

The platform of FIG. 1 also includes a stable illumination source for epifluorescence. Light source stabilization can be critical in image cytometry systems. While many other instruments (e.g., spectrophotometers and flow cytometers) are able to overcome this problem by monitoring and correcting source fluctuations, image cytometry is different because it is difficult to monitor and correct for the 250,000 or more detectors in a CCD camera. Accordingly, the source is constituted of a stable 100 W Hg vapor light source employing an optical fiber to scramble out the spatial variations (from arc wander), and feedback control to eliminate the remaining temporal instabilities [S Heynen, D A Gough, and J H Price. Optically stabilized mercury vapor short arc lamp as uv-light source for microscopy. In *Proceedings, International Society for Optical Engineering (SPIE), Optical Diagnostics of Biological Fluids and Advanced Techniques in Analytical Cytology*, volume 2982, pages 430-434, 1997]. The illumination stability provided is shown in FIG. 8. The gray trace is of an unstabilized lamp and the dark trace shows the result of feedback stabilization with our system. Both traces are envelopes showing the minimum and maximum intensity values recorded at 10 s intervals. The intensities were measured at 30 Hz using an Imaging Technology, Inc. Series 151 image processor. This long-term stability is exceptional. With feedback, the intensity coefficient of variation was reduced by over 30 times. This intensity control will greatly improve measurements that depend directly on the fluorescence intensity, such as in cell functional assays.

Figure 9:
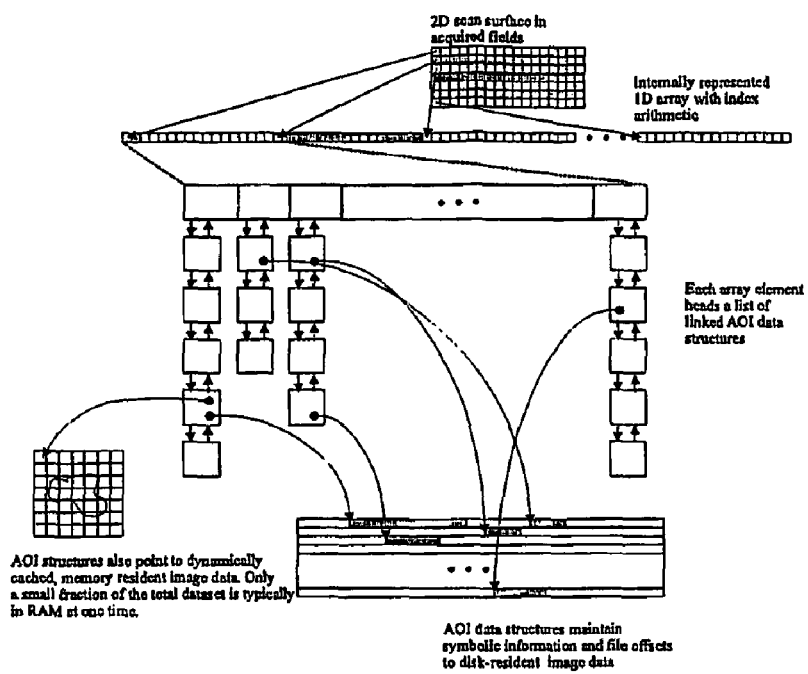
FIG. 9 is an illustration of an image table data structure which may be used in the practice of this invention.
Figure 10:
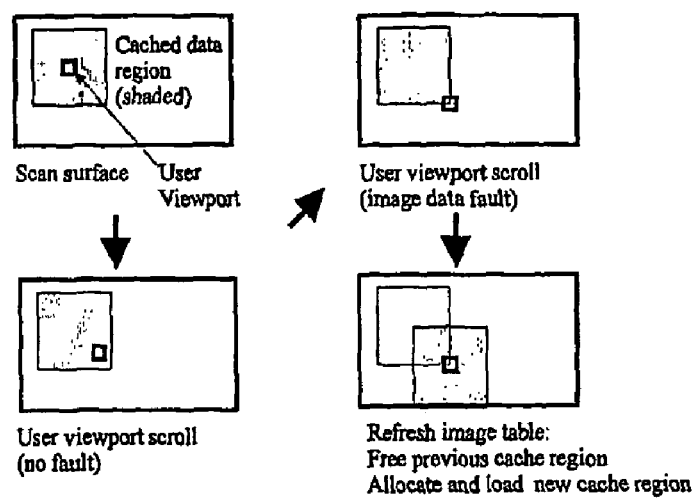
FIG. 10 is an illustration of an image table caching algorithm which may be used in the practice of this invention.

The invention further utilizes image area-of-interest (AOI) data structures and caching algorithms. One aspect of scanning cytometry is that the inherent view of the data is a contiguous image of the slide sample, composed of tens of thousands of microscope fields and gigabytes of raw image data (typically larger than the conventional 32-bit addressable space). Efficient access to AOIs in these data is required by both front-end users through the graphical interface, and by application programmers and assay developers. This access can only be provided by novel image data structures and caching algorithms that organize disk-resident AOIs in the scanned sample, and shuffle them in and out of RAM as required. An "image table" data structure has been developed [E A Hunter, W S Callaway, and J H Price. A software framework for scanning cytometry. In *Proceedings, International Society for Optical Engineering (SPIE), Optical Techiniques in Analytical Cytology IV*, San Jose, Calif., volume 3924, pages 22-28, January 2000.] to organize and manage image data for efficient access by the most prevalent use scenarios, including continuous (user scrollable), discontinuous (arbitrary rectangle), and database driven (query response) sample browsing and queries. FIGS. 9 and 10 illustrate designs for AOI metadata structures and associated caching algorithms. The image table is responsible for image area-of-interest management in a format designed to facilitate efficient AOI recall based on viewport overlay geometry. Efficient caching algorithms move disk-resident AOI data into RAM as needed. This allows for user browsing or sequential access of tens of gigabytes of image data or more on standard PC workstations.

Automated Fluorescence Microscopy for Cell Functional Analysis in a Cytoplasm-to-Nucleus NFκB Translocation Study This section describes the results of a study to quantify the subcellular distribution of the regulatory protein nuclear factor κB (NFκB) in response to cellular stimulation. Upon stimulation, for example by proinflammatory cytokines, the NFκB's inhibitory subunit is phosphorylated and subsequently destroyed by proteasomes. Loss of the inhibitory subunit frees the modified protein's p65 regulatory subunit to translocate from the cytoplasm into the nucleus where it can activate defense genes in response to the external stimulation.

Accurate and precise subcellular quantification of immunofluorescently labeled NFκB from microscope images provides a direct means of assessing the ability of a compound to inhibit cellular function in the presence of stimulation. This study examines cytoplasm-to-nucleus NFκB translocation in HUVEC cells in response to tumor necrosis factor α (TNFα), as an archetype of an image-based, cell functional assay. Because any other cellular compartments can be isolated and precisely quantified by specific immunofluorescent labeling working in tandem with the image acquisition and analysis technology described above, the speed and precision advantages demonstrated here are generally available to cell functional assays. The experiments also allow direct comparison of the results achieved by practice of our invention using the platform of FIG. 1 against previously-published results using different technology [G Ding, P Fischer, R Boltz, J Schmidt, J Colaianne, A Gough, R Rubin, and D Uiller. Characterization and quantitation of NFκB nuclear translocation induced by interleukin-1 and tumor necrosis factor-α. *Journal of Biological Chemistry*, 273(44):28897-28905, 1998] as measured by fidelity and system throughput. We show comparisons of cell compartment measurements in a substantially reduced well-population standard deviation, which is a function of both measurement technology and inherent biological heterogeneity. We show how response variability translates into reductions in the number of cells required to reliably detect fractional responses, and also how it affects inhibitor response estimates (via a Monte Carlo simulation of a model response $IC_{50}$ distribution). The ability to segregate cell images based on morphological information leads to further improvements by focusing measurement on a homogeneously responding subpopulation. Scanning and analysis are then validated by analyzing the response of three BIPI translocation inhibitor compounds. Finally, system throughput is explained and estimated scan rates are given for typical experimental parameters.

Experimental Procedures

The cells used in these studies were primary human umbilical vein endothelial cells (HUVEC) obtained from Clonetics Corporation. The cells were maintained in culture under standard conditions and passaged using Clonetics' proprietary EGM medium and reagent system. Since they are not transformed, HUVECs, generally become senescent after nine or ten passages. Cells used in these studies were from earlier passages and did not exhibit senescence associated morphological changes.

Prior to assay, cells were transferred to 96-well plates (Packard black ViewPlate) and incubated overnight to yield cell monolayers that were approximately 25% confluent. Plates used to determine a statistically optimal cell density for the assay were made by seeding wells at 5000, 2500, and 1000 cells per well and incubating overnight. Three selected compounds were tested for inhibition of TNFα stimulated NFκB translocation in HUVEC. The three compounds and controls were laid out in the plates as shown in Tables 2 and 3. Test compounds were directly diluted from DMSO stock solutions into medium to yield 60 mM compound solutions containing less than 0.7% DMSO. These solutions were serially diluted in medium to generate compound concentrations as low as 0.1 mM. After the medium was removed from the test plate, 100 µl aliquots of each compound dilution were dosed into triplicate wells. Unstimulated and TNFα stimulated control wells received 120 and 100 µl of medium, respectively. The cells were pre-incubated for 30 minutes at 37° C. before they were stimulated by adding 20 ml of TNFα (1200 U/ml medium) to each well. The final stimulating concentration of TNFα used in this assay was 200 U/ml. After 15 minutes incubation, the cells were fixed with 3.7% formaldehyde and then processed by using the NFκB kit reagents and protocol obtained from Cellomics (Pittsburgh, Pa.) to stain for cellular NFκB. In brief, cells are permeabilized, washed, incubated with rabbit anti-NFκB primary antibody for 1 hour, washed, incubated with a secondary anti-rabbit IgG antibody-Alexa Fluor 488 conjugate for 1 hour, and washed again. Nuclei were stained with either Hoechst dye included in the secondary antibody solution or with DAPI. When used, DAPI was added in a final wash buffer solution at 100 to 400 ng/ml and kept in place during storage and examination. Translocation of NFκB from the cytoplasm to the nucleus was assessed by visual examination of sample wells with a confocal microscope system.

TABLE 2

Template for 96 well NFκB control plate.

| Row | Cells per Well |
|---|---|
| A | Blank |
| B | 5000 |
| C | 5000 |
| D | 2500 |
| E | 2500 |
| F | 1000 |
| G | 1000 |
| H | Blank |

Rows B, D, F unstimulated;
rows C, E, G stimulated with 200 U/ml TNFα for 15m.

TABLE 3

Template for 96 well BIPI inhibitor plate.

| Row | Rows 1-3 | Rows 4-6 | Rows 7-9 | Rows 10-12 |
|---|---|---|---|---|
| A | 200 U/ml TNFα | 200 U/ml TNFα | Unstimulated | Unstimulated |
| B | 0.1 μM A | 0.1 μM B | 0.1 μM C | Blank |
| C | 0.3 μM A | 0.3 μM B | 0.3 μM C | Blank |
| D | 1 μM A | 1 μM B | 1 μM C | Blank |
| E | 3 μM A | 3 μM B | 3 μM C | Blank |
| F | 10 μM A | 10 μM B | 10 μM C | Blank |
| G | 30 μM A | 30 μM B | 30 μM C | Blank |
| H | 60 μM A | 60 μM B | 60 μM C | Blank |

Row A controls: stimulated with 200 U/ml TNFα for 15m. (columns 1-6), unstimulated (columns 7-12).
Rows B-H: triplicate wells of compounds A, B and C, at 0.1, 0.3, 1, 3, 10, 30, 60 μM concentrations.

The high-throughput microscopy platform illustrated above in FIG. 1 was used to automate fluorescent image acquisition and analysis of the NFκB assay. The primary system components consist of a standard fluorescent inverted microscope (a NIKON® TE-300 microscope); a Pentium III workstation; a control system, which houses the many electronic components; and software which controls the system for acquisition and analyzes the acquired images. The objective used in the scan was a NIKON® CFI60 20×.5NA Plan Fluor objective. The spatially and temporally stabilized fluorescent light source is a uses a 100 watt Osram HBO 103 W/2 mercury arc lamp as its light source and connects to the microscope at the NIKON® epi-fluorescent attachment. A standard Chroma Dapi/Hoechst filter cube with a long pass emission filter was used for the nuclear channel. A standard FITC filter cube with a long pass emission filter was used for the Alexa488-labeled NFκB channel. A Cohu 640×480 pixel 10-bit progressive camera (model 6612-3000; 9.9 μm² pixels) was used for image acquisition.

Measurement of Distributions or Fractional Localized Intensities (FLI) of Subcellular Compartments Cellular substances are dynamically distributed during cellular responses. Although there may be hundreds of thousands to millions of different cellular substances, a cellular response can be measured by specifically labeling the subset of substances participating in the response. At any point in time, the combination of compartment identification and specifically labeled substances can be used to take a snapshot of the distributions. Image segmentation creates the image masks for each cellular compartment. For example, a least-squares-designed contrast-enhancing filter is used on each of the cellular compartment images to create segmentation masks. The nuclear segmentation is then used as a guide to separate overlapping compartments using tessellation. These image segmentation techniques work best on many types of cellular images. But other segmentation techniques can also be used to generate the segmented masks for each cellular compartment The measurement logic then loops through each set of pixels identified by the compartment masks and sums pixel intensities I(x; y). As an example, assume membrane, cytoplasmic and nuclear masks, m, c and n, respectively, with sizes $N_c$, $N_n$ and $N_m$. The distributions over the compartments are defined as the fractional localized intensities of each compartment. The fractional localized intensity of the cytoplasm $F_c$ is $$F_c = \frac{\sum_{(x,y) \in c} I(x, y)}{\sum_{(x,y) \in c,m,n} I(x, y)} \qquad (1)$$

The equations are analogous for the fractional localized intensities of the nucleus $F_n$ and membrane $F_m$, and $F_c+F_n+F_m=1$. The physics of fluorescence image formation leads to the use of integrated intensity to quantify cellular distributions. The emission intensity at pixel location (x, y) in an image plane is $$I(x, y) = \int_0^z I_0 Q\varepsilon u\, dz = I_0 Q\varepsilon u' z \qquad (2)$$

with incident (excitation) intensity $I_0$, quantum yield Q, extinction coefficient $\varepsilon$, local and column average fluorophore concentrations u and u', and column thickness z. When the depth of field is greater than the cell, image formation effectively integrates the sample in z, the direction of the optical axis. When the depth of field is smaller than the cell as with high NA, confocal and multiphoton optics, explicit integration in z may more accurately represent the intensity. Assuming this integration has already taken place either optically with large depths of field or computationally with small depths of field, intensity measurements integrate in the orthogonal dimensions $$\sum_{(x,y)} I(x, y) = I_0 Q\varepsilon \sum_{(x,y)} u'(x, y) z(x, y) \qquad (3)$$

which has units proportional to moles fluorophore. $F_c$ becomes $$F_c = \frac{\sum_{(x,y) \in c} u'(x, y) z(x, y)}{\sum_{(x,y) \in c} u'(x, y) z(x, y) + \frac{Q_n}{Q_c} \sum_{(x,y) \in n} u'(x, y) z(x, y) + \frac{Q_m}{Q_c} \sum_{(x,y) \in m} u'(x, y) z(x, y)} \qquad (4)$$

with units of moles fluorophore. As before, the equations are analogous for the fractional localized intensities of the nucleus $F_n$ and membrane $F_m$. Quantum yields are potentially compartment specific (i.e., vary with pH, ion concentration and other local physical parameters) and can be established experimentally as part of protocol development. Note that direct integration over the compartment image segments is preferred over average compartment intensity ratios or differences used in U.S. Pat. No. 5,989,835 because a ratio of areas causes a bias factor that confounds direct interpretation unless $N_c=N_n=N_m$, which can only be artificially achieved by discarding a majority of the cytoplasm and nuclear signal because typically $N_c, N_n > Nm$. The cellular (or subcellular compartment) area is a function of height even when volume is fixed The same amount of a cellular substance can be distributed over different volumes or areas. Averaging the intensities over the areas thus introduces a dependence on something that has nothing to do with the amount of the labeled substance. Note also that in equations (1) and (4) $F_c$ is the fraction of the total integrated fluorescence over all of the compartments, rather than the fraction of one compartment to the other.

Generalizing further, a compartment k in an arbitrary number $\eta$ of compartments $\zeta$ has fractional localized intensity $$F_{\zeta_k} = \frac{\sum_{(x,y)\in\zeta_k} I(x,y)}{\sum_{i=1}^{\eta}\sum_{(x,y)\in\zeta_i} I(x,y)} \text{ and } \sum_{i=1}^{\eta} F_{\zeta_i} = 1 \qquad (5a)$$

Similarly, any subset of compartments can be combined by addition to produce multi-compartment fractional localized intensities. For example, the fractional localized intensity of compartments 1 and 3 is $$F_{\zeta_{1,3}} = F_{\zeta_1} + F_{\zeta_3} \qquad (5b)$$

and so on.

Results and Error in the FLIC

Figure 11:
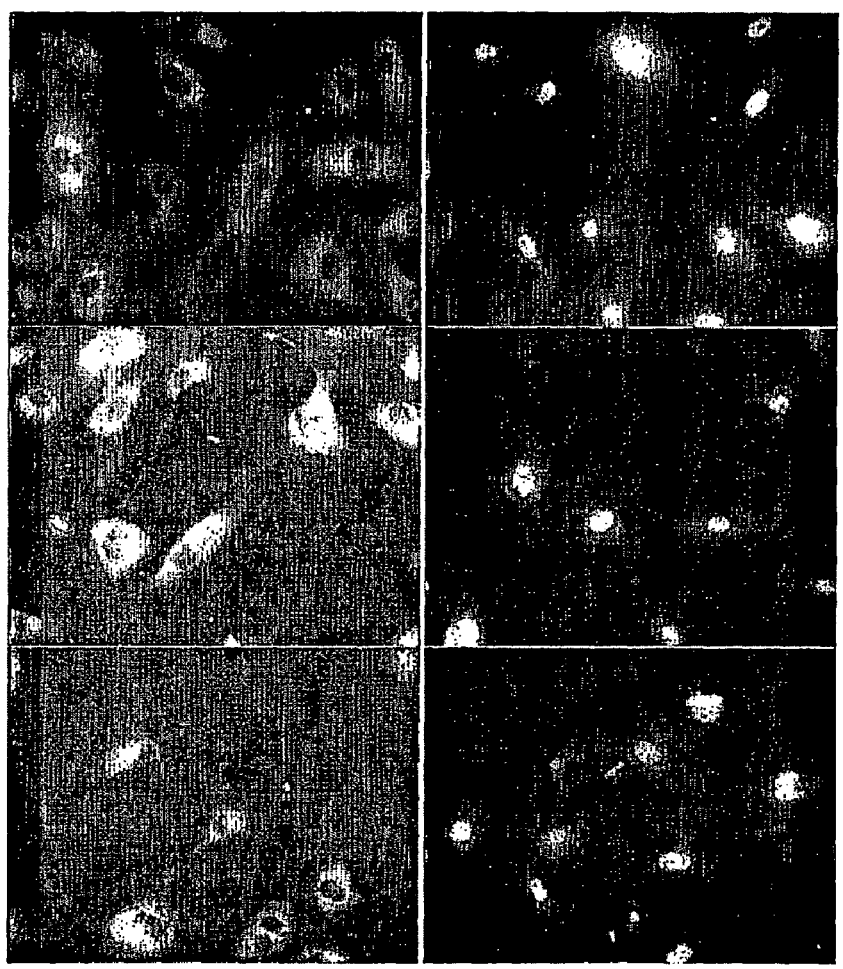
FIG. 11 is a series of three panels of magnified cell images showing the effect of multichannel image acquisition and processing software components on a BIPI-prepared well-plate.

Fractional Localized Intensity Measurements on TNFα-induced NFκB Cytoplasm-Nucleus Translocation: Immunofluorescent staining of the NFκB p65 regulatory subunit allows for easy characterization of the intercellular NFκB distribution by visual inspection of images acquired during scanning. The majority of fluorescence lies outside the nuclear area in unstimulated cells, while a substantial amount co-locates with the nuclear mask subsequent to maximal stimulation with TNFα (FIG. 11). The panels of FIG. 11 show translocation of cytoplasmic NFκB p65 regulatory subunit (unstimulated; left images) to cell nucleus (stimulated; right images) subsequent to stimulation of HUVEC cells with TNFα. Cell densities were 5000 cells/well (top; rows B,C), 2500 cells/well (center; rows D,E) and 1000 cells/well (bottom; rows F,G). A clear majority of Alexa488-labeled p65 resides ubiquitously in the cytoplasm before stimulation, while bound to the inhibitory subunit. Stimulation with TNFα causes phosphorylation and separation of p65 from the inhibitory subunit, allowing for translocation to occur. Only ≈20% of gross p65 translocates upon maximal stimulation (qualitative visual inspection of images tends to overemphasize the higher fluorophore concentration in the nuclei of stimulated cells, and suggest a greater translocation). Note how background fluorescence varies between wells. As stipulated in previous reports, the fraction of p65 to translocate on stimulus represents ≈20% of the gross amount contained in unstimulated cell cytoplasm. [Ding et al.]. Effects due to background fluorescence are corrected by estimating and subtracting the mean background image intensity, which was found to be approximately constant from image-to-image, but can vary from well-to-well. Therefore, corrections were performed on a per well basis.

Co-location of p65 immunofluorescence with the nuclear mask can occur in unstimulated cells as image formation integrates the p65-bound fluorophore emission through the three dimensional sample parallel to the optical axis, and therefore is susceptible to contribution above or below the nuclear volume. Similarly, stimulated cell images carry residual cytoplasmic p65 immunofluorescence contributions co-located with the nuclear mask. Although this effect may be small it introduces a bias in fractional localized intensity measurements. For applications where this effect is not negligible, a correction procedure could be developed by correlating nuclear and cytoplasm absolute integrated intensities in unstimulated cells to establish the average contribution of cytoplasm resident fluorophore to nuclear measurements as a function of cytoplasmic intensity.

Figure 12:
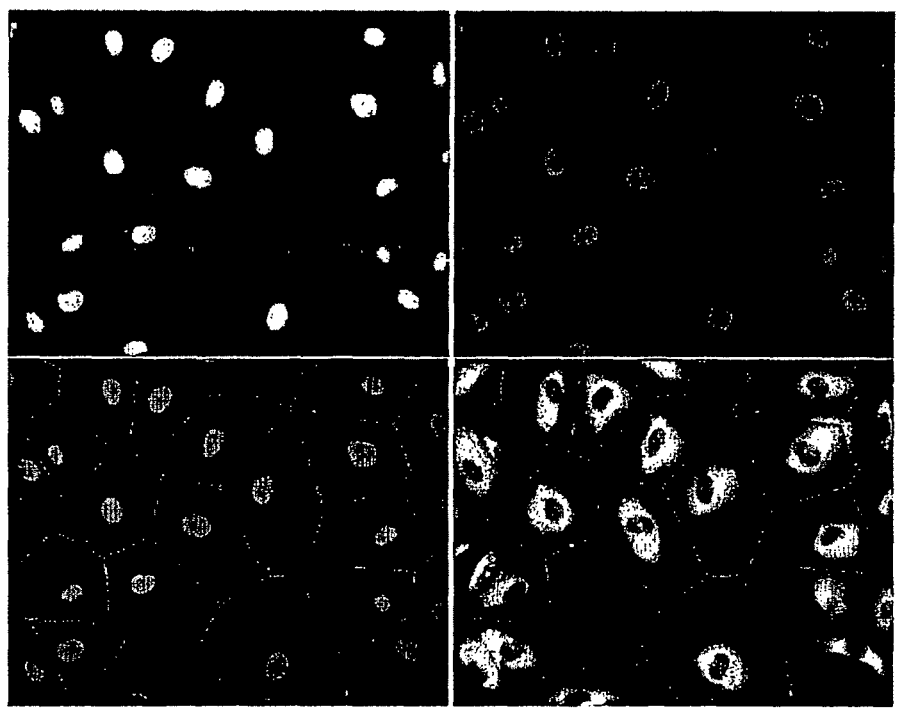
FIG. 12 includes four panels showing how image segmentation and tessellation may be used in the invention to identify and localize cell nuclei.

FIG. 12 illustrates image acquisition processing stages in the system of FIG. 1. To obtain the images of FIG. 12, the nuclear channel (Hoechst 33342 or DAPI) was scanned over the 10×10 field area in each well to populate the image table with nuclear intensity images (upper left). The upper right panel shows the associated nuclear mask images produced by filtering and intelligent thresholding of the in-focus acquired images. Subjectively, masks are consistent with the quantitative study conducted by Price, Hunter, and Gough, which demonstrated accurate and precise nuclear masks despite significant local image variations and a wide range of nuclear intensities from cell-to-cell. Such variations can confound simple techniques, because the accuracy and precision of the resulting masks would substantially bias localized intensity measurements. Using human-segmented training and testing data, this filtering technique has been shown to achieve accuracy >93% correct classification of pixels and precision of less than about 1% coefficient of variation [Price, Hunter, and Gough]. This is acceptable, and perhaps a limiting performance level, since human-human agreement in manually segmented examples is likely to be comparable. The scan area tessellated by nuclear centroids is shown in FIG. 12 (lower left). This tessellation structure is then used to dynamically assemble and associate the quantitative p65 channel (Alexa488) with the individual nuclear images (lower right). Reliable alignment between channels provides the basis for accurate fractional localized intensity measurements.

In FIG. 12, individually addressable images of Hoechst 33342- or DAPI-labeled cell nuclei were identified and extracted from the image stream produced during scanning. These images were saved to disk using an image table data structure (FIG. 9) that maintains the relative positions of each nuclei (upper left). Binary nuclear mask images (upper right) show the accuracy of the nuclear segmentation processing achieved, which is critical for compartment localized measurements. Voronoi tessellation of nuclear centroids (lower left) partitioned the data structure and scan area into polygonal regions used to correlate subsequent channels with individual nuclei dower right), in order to maximize the signal from every cell.

Figure 13:
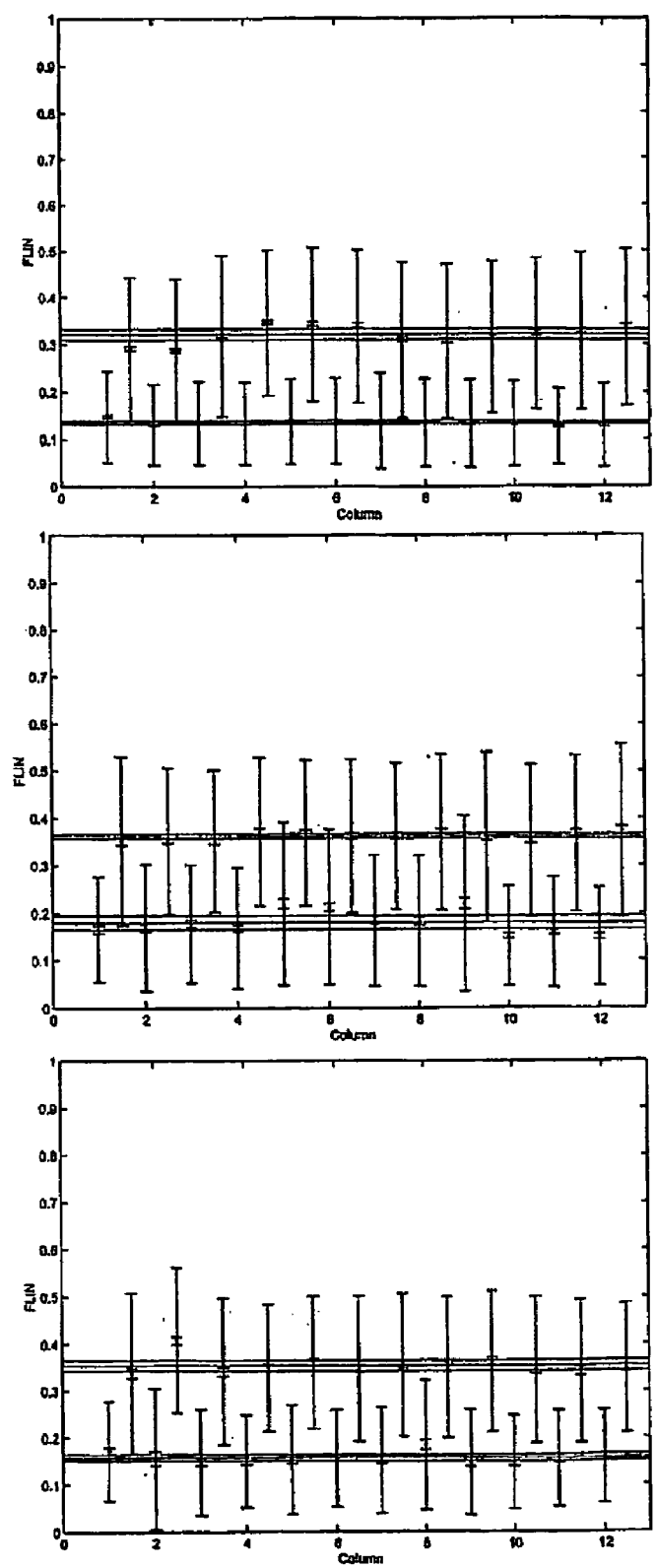
FIG. 13 illustrates the population statistics for TNFα-induced NFκB activation in HUVEC cells.

Maximal NFκB translocation following 200 U/ml TNFα stimulation of HUVEC cells was quantified by measuring fractional localized intensity in the nucleus (FLIN) (fractional localized intensity in the cytoplasm (FLIC) is equivalent in the two-compartment translocation model used in this study. FLIC+FLIN=1) for every cell completely within the scan area (Table 4). At the different cell densities, FLIN sample mean, standard deviation ($\sigma$), standard error (SE) and coefficient of variation (CV) were calculated in 12 replicate wells (Table 4). Well-to-well sample statistics for all six density×stimulation treatments of the within-well sample mean FLINs are reported in Table 5, and illustrated by the constant horizontal lines in FIG. 13. FIG. 13 illustrates the population statistics for TNFα-induced NFκB activation in HUVEC cells. FLIN response ($\mu \pm 2\sigma$) is plotted per well for unstimulated (lower FLIN) and maximally stimulated (increased FLIN) cells (200 U/ml TNFα) for 5000 cells/well (top; rows B,C), 2500 cells/well (center; rows D,E) and 1000 cells/well (bottom; rows F,G). The horizontal lines give across row mean-of-means±2×SE.

gives a 4 SE empirical response resolution of 0.0139 FLIN increments, or about 7.4% increments over the 18.80% signal dynamic range.

By analyzing the spread of well-average FLIN measurements from well-to-well, we can assess well-to-well variability and repeatability of the experiment. The row aggregate FLIN sample means, calculated by averaging the 12 replicate well sample means in each row, have a standard error of $1.6 \times 10^{-3}$-$7.20 \times 10^{-3}$ (CV of 2.34% -13.93%) (Table 5). This well-to-well sample mean variability is visualized by the horizontal aggregate mean and±2SE lines in FIG. 13. Devia-

TABLE 4

Well-wise and row-pooled FLIN statistics. CVs defined as (std dev)/mean

| Well | n | mean | σ | SE | CV | Well | n | mean | σ | SE | CV |
|---|---|---|---|---|---|---|---|---|---|---|---|
| 1B | 964 | 0.147846 | 0.048122 | 0.001550 | 0.325484 | 1C | 1123 | 0.290729 | 0.075713 | 0.002259 | 0.260423 |
| 2B | 1132 | 0.130526 | 0.042521 | 0.001264 | 0.325768 | 2C | 1226 | 0.286024 | 0.076772 | 0.002193 | 0.268410 |
| 3B | 1309 | 0.134470 | 0.043876 | 0.001213 | 0.326291 | 3C | 1443 | 0.318096 | 0.085135 | 0.002241 | 0.267640 |
| 4B | 1263 | 0.132990 | 0.043633 | 0.001228 | 0.328090 | 4C | 1265 | 0.346417 | 0.077291 | 0.002173 | 0.223114 |
| 5B | 1089 | 0.137363 | 0.045115 | 0.001367 | 0.328437 | 5C | 1410 | 0.342634 | 0.081898 | 0.002181 | 0.239025 |
| 6B | 1297 | 0.138022 | 0.045132 | 0.001253 | 0.326990 | 6C | 1149 | 0.338905 | 0.081211 | 0.002396 | 0.239627 |
| 7B | 1251 | 0.138558 | 0.050421 | 0.001426 | 0.363893 | 7C | 1367 | 0.309078 | 0.082221 | 0.002224 | 0.266019 |
| 8B | 1153 | 0.134308 | 0.046321 | 0.001364 | 0.344884 | 8C | 1330 | 0.305640 | 0.081423 | 0.002233 | 0.266401 |
| 9B | 1283 | 0.132846 | 0.046153 | 0.001289 | 0.347419 | 9C | 1260 | 0.314321 | 0.080458 | 0.002267 | 0.255975 |
| 10B | 1127 | 0.132862 | 0.044833 | 0.001335 | 0.337442 | 10C | 1311 | 0.322215 | 0.080099 | 0.002212 | 0.248589 |
| 11B | 994 | 0.126178 | 0.040244 | 0.001276 | 0.318942 | 11C | 1108 | 0.328182 | 0.083463 | 0.002507 | 0.254319 |
| 12B | 1234 | 0.129016 | 0.043913 | 0.001250 | 0.340366 | 12C | 1044 | 0.336819 | 0.082491 | 0.002553 | 0.244912 |
| Row B | 14096 | 0.1345 | 0.0454 | 0.0004 | 0.3374 | Row C | 15036 | 0.3199 | 0.0829 | 0.0007 | 0.2592 |
| 1D | 192 | 0.165380 | 0.055521 | 0.004007 | 0.335721 | 1E | 488 | 0.350998 | 0.088568 | 0.004009 | 0.252331 |
| 2D | 228 | 0.169188 | 0.066621 | 0.004412 | 0.393770 | 2E | 533 | 0.352654 | 0.076766 | 0.003325 | 0.217679 |
| 3D | 273 | 0.177909 | 0.062334 | 0.003773 | 0.350374 | 3E | 591 | 0.350479 | 0.074646 | 0.003071 | 0.212983 |
| 4D | 330 | 0.167759 | 0.063749 | 0.003509 | 0.380006 | 4E | 562 | 0.371006 | 0.077932 | 0.003287 | 0.210056 |
| 5D | 356 | 0.219419 | 0.086005 | 0.004558 | 0.391968 | 5E | 615 | 0.368168 | 0.077079 | 0.003108 | 0.209359 |
| 6D | 367 | 0.211853 | 0.082027 | 0.004282 | 0.387188 | 6E | 589 | 0.361919 | 0.080731 | 0.003326 | 0.223064 |
| 7D | 349 | 0.184329 | 0.069234 | 0.003706 | 0.375601 | 7E | 594 | 0.361462 | 0.077352 | 0.003174 | 0.213998 |
| 8D | 319 | 0.183501 | 0.068811 | 0.003853 | 0.374990 | 8E | 542 | 0.369526 | 0.081884 | 0.003517 | 0.221593 |
| 9D | 311 | 0.219387 | 0.092681 | 0.005255 | 0.422455 | 9E | 622 | 0.359408 | 0.089347 | 0.003473 | 0.248594 |
| 10D | 382 | 0.150226 | 0.052488 | 0.002686 | 0.349390 | 10E | 644 | 0.352375 | 0.079729 | 0.003142 | 0.226263 |
| 11D | 354 | 0.158436 | 0.058115 | 0.003089 | 0.366802 | 11E | 534 | 0.367225 | 0.082335 | 0.003563 | 0.224207 |
| 12D | 277 | 0.149743 | 0.051306 | 0.003083 | 0.342629 | 12E | 396 | 0.374030 | 0.091069 | 0.004576 | 0.243482 |
| Row D | 3738 | 0.1809 | 0.0735 | 0.0006 | 0.4062 | Row E | 6750 | 0.3613 | 0.0816 | 0.0010 | 0.2259 |
| 1F | 199 | 0.171691 | 0.052991 | 0.003756 | 0.308639 | 1G | 279 | 0.336876 | 0.086114 | 0.005155 | 0.255624 |
| 2F | 109 | 0.154424 | 0.075078 | 0.007191 | 0.486179 | 2G | 332 | 0.406467 | 0.077388 | 0.004247 | 0.190391 |
| 3F | 204 | 0.147685 | 0.056180 | 0.003933 | 0.380404 | 3G | 306 | 0.340068 | 0.078636 | 0.004495 | 0.231235 |
| 4F | 182 | 0.149932 | 0.049610 | 0.003677 | 0.330882 | 4G | 296 | 0.348505 | 0.068383 | 0.003975 | 0.196218 |
| 5F | 177 | 0.153247 | 0.058143 | 0.004370 | 0.379411 | 5G | 310 | 0.359116 | 0.070316 | 0.003994 | 0.195803 |
| 6F | 174 | 0.155897 | 0.051656 | 0.003916 | 0.331348 | 6G | 339 | 0.346658 | 0.077604 | 0.004215 | 0.223862 |
| 7F | 200 | 0.151608 | 0.056382 | 0.003987 | 0.371893 | 7G | 329 | 0.354841 | 0.075766 | 0.004177 | 0.213521 |
| 8F | 172 | 0.183963 | 0.068814 | 0.005247 | 0.374063 | 8G | 290 | 0.349761 | 0.074941 | 0.004401 | 0.214263 |
| 9F | 163 | 0.146976 | 0.056036 | 0.004389 | 0.381262 | 9G | 281 | 0.362283 | 0.075045 | 0.004477 | 0.207145 |
| 10F | 171 | 0.146951 | 0.049964 | 0.003821 | 0.340006 | 10G | 292 | 0.344575 | 0.077994 | 0.004564 | 0.226347 |
| 11F | 176 | 0.155161 | 0.051188 | 0.003858 | 0.329902 | 11G | 317 | 0.341355 | 0.076450 | 0.004294 | 0.223961 |
| 12F | 160 | 0.158985 | 0.049600 | 0.003921 | 0.311977 | 12G | 235 | 0.347623 | 0.069314 | 0.004522 | 0.199394 |
| Row F | 2087 | 0.1564 | 0.0570 | 0.0012 | 0.3642 | Row G | 3606 | 0.3537 | 0.0779 | 0.0013 | 0.2203 |

We measured the occurrence of 18.18% -19.68% (18.80% average) translocation of labeled NFκB, which we calculated by averaging the 12 row replicate well FLIN sample means per row, and differencing stimulated and unstimulated averages at each cellular density. Heterogeneity of cellular response to TNFα0 stimulation is apparent by visual inspection of acquired images and summarized in the ±2σ confidence interval widths in FIG. 13 (the larger interval around each well mean). Stimulated and unstimulated well populations have significant overlap in response. However, the average response of 18.80% is large compared to the FLIN standard errors which are calculated within wells in Table 4 and shown graphically in FIG. 13 (smaller interval about each well mean). For example, the average SE in row E, $3.46 \times 10^{-3}$, tions of the individual well responses from this region show the effect of protocol perturbations in individual well environments. Although statistically significant differences exist, the physical or scientific significance in terms of effect on measured translocation is typically small in this experiment, indicating the possibility of limiting the number of replicate wells required in an optimized and controlled protocol. As a quantitative example, a trimmed between-well CV for row D in Table 4 reduces variability from 13.93% to 4.76%. Note that row D had the highest CV and that the numbers were trimmed to the six median wells (using the assumption that those wells with the most human preparation error were at the tails of the distribution). Wellplate replicate layout to mitigate the effect of well-to-well variability must be determined during specific assay development.

TABLE 5

Well-to-well statistics of well-average FLIN values (n = 12).
Mean, standard deviation, standard error and coefficient of variation
of the FLIN well sample means across each row.

| Row | mean   | σ      | SE     | CV     |
|-----|--------|--------|--------|--------|
| B   | 0.1346 | 0.0055 | 0.0016 | 0.0412 |
| C   | 0.3199 | 0.0198 | 0.0057 | 0.0618 |
| D   | 0.1798 | 0.0250 | 0.0072 | 0.1393 |
| E   | 0.3616 | 0.0085 | 0.0024 | 0.0234 |
| F   | 0.1564 | 0.0110 | 0.0032 | 0.0704 |
| G   | 0.3532 | 0.0184 | 0.0053 | 0.0521 |

Automatic Determination of Cells/Well Required to Reach a Minimum Significant Response Theory of Dose Response Resolution: To underpin the empirical dose response resolution theoretically and to properly stage a baseline comparison of the data with results produced using a different technology, an objective definition of the meaning of response resolution and its dependence on measurement fidelity, sample size and error controls is needed. Inhibitory responses are estimated by nonlinear regression from a collection of experimental well-average measurements distributed across a range of inhibitor concentrations. Sources of variability in curve estimates include high population variability (heterogeneity) in response, well-to-well variability and inadequate sampling of inhibitor concentration. These factors are naturally dependent; measurement precision places limitations on measurable differences in response. Experiment design involves optimizing jointly over well datapoint replicates and individual well measurement quality (a function of the number of cells per well).

A direct measure of system resolution is the minimum statistically significant response that can be reliably measured. An equivalent measure of system performance is, for a specific minimum significant response implicated by choice of inhibitory response model, the number of cell measurements required at each inhibitor concentration to reliably estimate the response model parameters. For two populations of responding cells, we want to determine the minimum difference in mean FLIN that can be reliably detected as a measure of system resolution. For this, we define a two-sample hypothesis test $$H_0 : \mu_1 - \mu_2 = 0 \quad (6)$$

$$H_\alpha : \mu_1 - \mu_2 > 0 \quad (7)$$

where $\mu_1$ and $\mu_2$ are the true (unobserved) mean FUN responses, and $H_0$ and $H_\alpha$ are the null and alternative hypotheses. This is an upper-tailed test with decision rule $z > z_\alpha$, where $z = (x_1 - x_2)/(\sigma\sqrt{2/n})$ is the unit variance normalized test statistic for sample means $x_1$ and $x_2$, and $z_\alpha$ is the threshold for rejection of an α-level test, $$\alpha = Pr(z > z_\alpha \mid H_0) = 1 - \int_{-\infty}^{z_\alpha} \frac{1}{\sqrt{2\pi}} e^{-\frac{x^2}{2}} dx = 1 - \Phi(z_\alpha) \quad (8)$$

The type I error probability (α) is the likelihood that two identically inhibited samples will, by natural variations, show a minimally significant response difference in measurements). The probability of Type I errors is controlled by fixing its value in advance, e.g. α=0.05, as determined by assay requirements. Similarly, the type II error probability (β) is the likelihood that two samples with minimally different responses will not show a significant difference in measurements, and it is similarly determined and fixed by assay requirements. To relate these assay parameters and derive a measure of precision, we express the probability β mathematically, assuming an absolute minimum significant response (MSR) Δμ

$$Pr(z < z_\alpha \mid \mu_1 - \mu_2 = \Delta\mu) = \beta(\Delta\mu) \quad (9)$$

$$Pr\left(\frac{x_1 - x_2 - \Delta\mu}{\sigma\sqrt{2/n}} < z_\alpha - \frac{\Delta\mu}{\sigma\sqrt{2/n}} \mid \mu_1 - \mu_2 = \Delta\mu\right) = \beta(\Delta\mu, \sigma, n) \quad (10)$$

$$\Phi\left(z_\alpha - \frac{\Delta\mu}{\sigma\sqrt{2/n}}\right) = \beta(\Delta\mu, \sigma, n) \quad (11)$$

This expresses β as a function of Δμ, or (FLIN population standard deviation) and n (sample size). The assumption that both populations share the same σ is reasonable because in the limit, the minimum detectable difference approaches the same population (formulae for the case $\sigma_1 \neq \sigma_2$ are easy to derive, however, when we need an estimate of sample size requirements for detecting very distinct responses). By specifying β as we did for α, e.g. α=β=0.05, we control type II error probability and fix $z_\beta$ $$\Phi(z_\beta) = \beta \quad (12)$$

$$z_\beta = z_\alpha - \frac{\Delta\mu}{\sigma\sqrt{2/n}} \quad (13)$$

$$\Delta\mu = (z_\alpha - z_\beta)\sigma\sqrt{2/n} \quad (14)$$

MSR is expressed as a fraction of the dynamic range of the assay or experiment $$MSR = \frac{\Delta\mu}{\mu_{max} - \mu_{min}} = \frac{(z_\alpha - z_\beta)\sigma\sqrt{2/n}}{\mu_{max} - \mu_{min}} \quad (15)$$

For specified MSR and assay parameters, the minimum corresponding sample size is $$n = 2\left(\frac{(z_\alpha - z_\beta)\sigma}{\Delta\mu MSR}\right)^2 \quad (16)$$

To gain an understanding of this precision measure, let α=β=0.05, then MSR is the minimum significant dose response relative to the assay dynamic range such that
1. There is a 95% chance that when there is no true difference between population mean responses, $z \leq z_\alpha$ or $x_1 - x_2 \leq z_\alpha \sigma\sqrt{2/n} = \Delta\mu/2$ (no significant difference measured between sample means), and
2. There is a 95% chance that when $\mu_1 - \mu_2 = \Delta\mu > 0$, $x_1 - x_2 > \Delta\mu/2$ (significant difference measured between sample means)

Therefore, specification of MSR and protocol parameters allows one to make objective guarantees about the minimum required sample size to control the variability of dose response point measurements so that they are unlikely to overlap (according to our specification of α, β). A family of n(MSR) curves are plotted in FIG. 14. The average population σ in row E is σ=8.1453×10$^{-2}$, which would allow a 7.4% MSR for n≈742.

The control of type I and II error probabilities in this scheme has different implications than most traditional hypothesis testing by virtue of its use as a measure of experimental precision. A type I error in an inhibitor assay indicates that the replicate measurements produced responses outside the experimentally set control interval. A type II error indicates that nonreplicate measurements (different inhibitor concentrations) produced measured responses within the same control interval. Nonlinear regression to an inhibitory response model will not discriminate the different meanings of these errors; only that they both produce datapoint scatter and complicate parameter estimation Therefore, for experiments involving inhibitory response, it is suggested to constrain $\alpha=\beta$.

Figure 14:
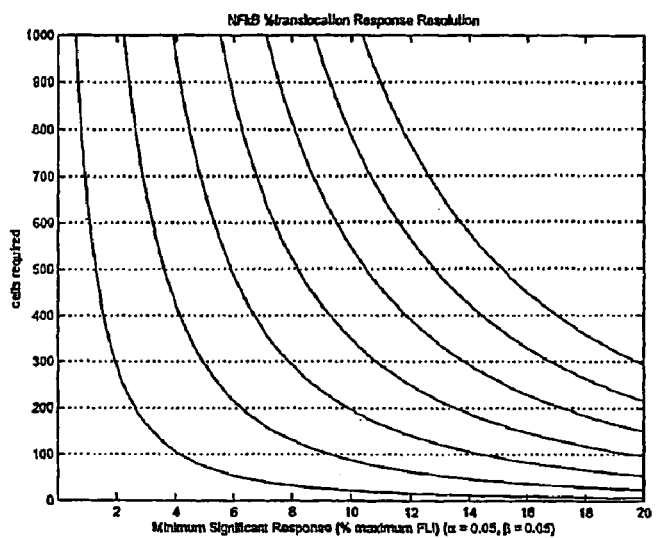
FIG. 14 is a family of curves representing the theoretical dose response resolution for σ={0.02,0.04,0.06,0.08,0.1, 0.12,0.14} (ascending, α=0.05 (Type I error probability), β=0.05 (Type II error probability)).

FIG. 14 is a curve family showing theoretical dose response resolution for $\sigma=\{0.02, 0.04, 0.06, 0.08, 0.1, 0.12,$ 0.14$\}$ (ascending, $\alpha=0.05$ (Type I error probability), $\beta=0.05$ (Type II error probability)). In this figure, the number of cells required (y axis) is plotted against the fraction of total NFκB translocation that is resolved (x axis). Measurements made according to this invention fall between $\sigma=0.06$ and $\sigma=0.08$ (between third and fourth curves from the bottom) as reported in Table 4. These relationships allow for easy visualization of the effect of improved or degraded measurement fidelity and resolution on cell number requirements.

Sample Size Requirements: Ding et al. [G Ding, P Fischer, R Boltz, J Schmidt, J Colaianne, A Gough, R Rubin, and D Uiller. Characterization and quantitation of NFκB nuclear translocation induced by interleukin-1 and tumor necrosis factor-α. *Journal of Biological Chemistry*, 273(44):28897-28905, 1998] report sample size requirements for similar NFκB translocation experiments carried out on an imaging platform. To demonstrate the superior cell measurement fidelity of the technology reported here, Table 6 compares the results published by Ding et al. against similar calculations based on the raw measurements data in Table 4 and the derivation in the previous subsection. Table 6 provides comparative estimates of the number of cellular measurements needed to measure a given level of stimulation response (from 2%-100% of the total translocation amplitude of about 19% FLIN change) as a function of NFκB fluorophore translocation at 95% and 99% type I confidences ($\alpha=0.05, 0.01$; $\beta=0.20$). The parameters of the experiment were duplicated here to provide a direct comparison on cellular measurement fidelity. Additional response level 2%-10% and an additional column ($\alpha=\beta=0.001$) were added to further demonstrate results according to our invention. In the general population, the same number of cells required to measure a 100% response (19% translocation event) using the technology reported in Ding et al. allowed a measurement of about 25% response using the principles of our invention. Reasonable dose response curve estimation may require a 20% resolution or better, which at $\alpha=0.05$, $\beta=0.20$ would require about 12× fewer measurements to achieve using the principles of our invention.

TABLE 6

Comparison of the minimum number of cells required to measure percent of the total (maximum stimulation) NFκB translocation (19% FLIN change) obtained with the invention with those reported in Ding et al., at controlled error probabilities (type I, type II). The response column gives the percent response of the full dynamic range of the measurement (18.8%). Our calculations assume well sample mean measurements Gaussian distributed, justified by Central Limit Theorem, for $n \geq 30$. For $n < 30$, student's t distribution is appropriate. However, for simplicity, a minimum of 30 cells is always measured. Our calculations assume $\Delta\mu = 0.1818$ and $\sigma$ linearly interpolated between 0.0650 (unstimulated) and 0.0800 (stimulated).

| % Maximum Response | Ding et al. (0.05, 0.20) | Invention (0.05, 0.20) | Ding et al. (0.01, 0.20) | Invention (0.01, 0.20) | Invention (0.001, 0.001) |
|---|---|---|---|---|---|
| 2% | Not given | 3970 | Not given | 6445 | 24528 |
| 5% | Not given | 640 | Not given | 1039 | 3952 |
| 10% | Not given | 162 | Not given | 263 | 1000 |
| 20% | >500 | 42 | >500 | 68 | 256 |
| 30% | 388 | <30 | >500 | 31 | 117 |
| 35% | 220 | <30 | 331 | <30 | 87 |
| 45% | 141 | <30 | 213 | <30 | 54 |
| 55% | 99 | <30 | 149 | <30 | 37 |
| 65% | 73 | <30 | 111 | <30 | <30 |
| 70% | 57 | <30 | 86 | <30 | <30 |
| 80% | 45 | <30 | 68 | <30 | <30 |
| 90% | 37 | <30 | 56 | <30 | <30 |
| 100% | 31 | <30 | 47 | <30 | <30 |

Figure 15:
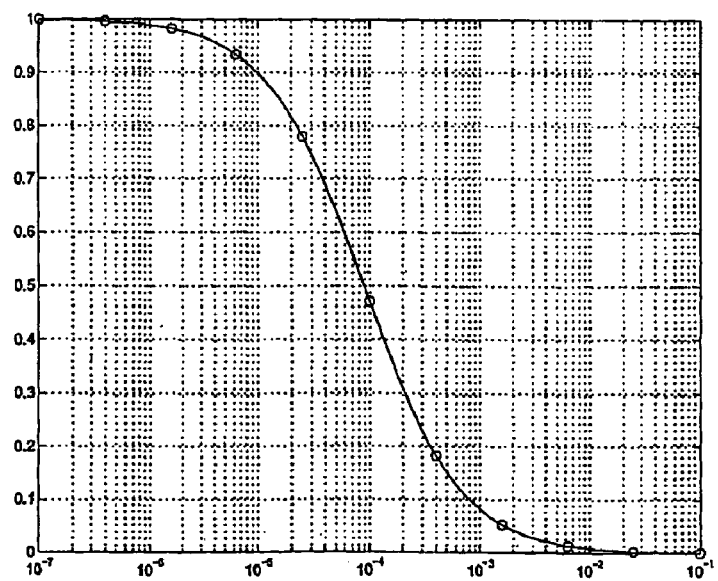
FIG. 15 shows a theoretical dose response curve with $\mu_{max}=1.0$, $\mu_{min}=0.0$, and $IC_{50}=8.895\times10^{-5}$.
Figure 16:
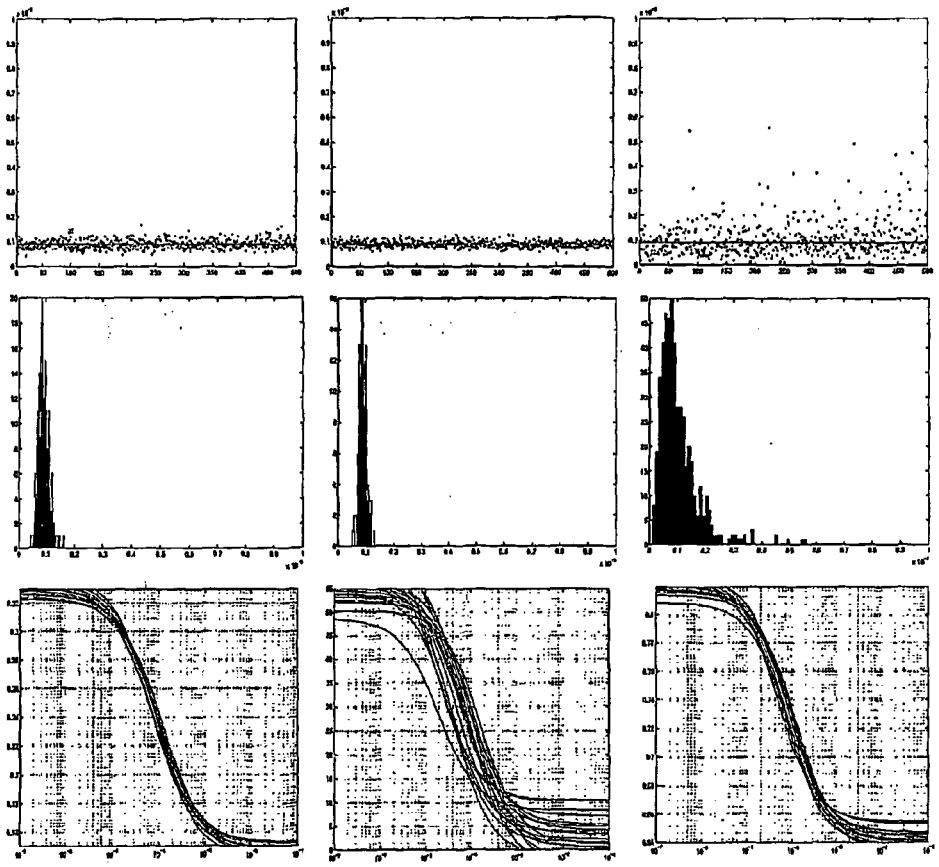
FIG. 16 is a family of plots showing a worst-case response for well-well mean FLIN response.
Figure 17:
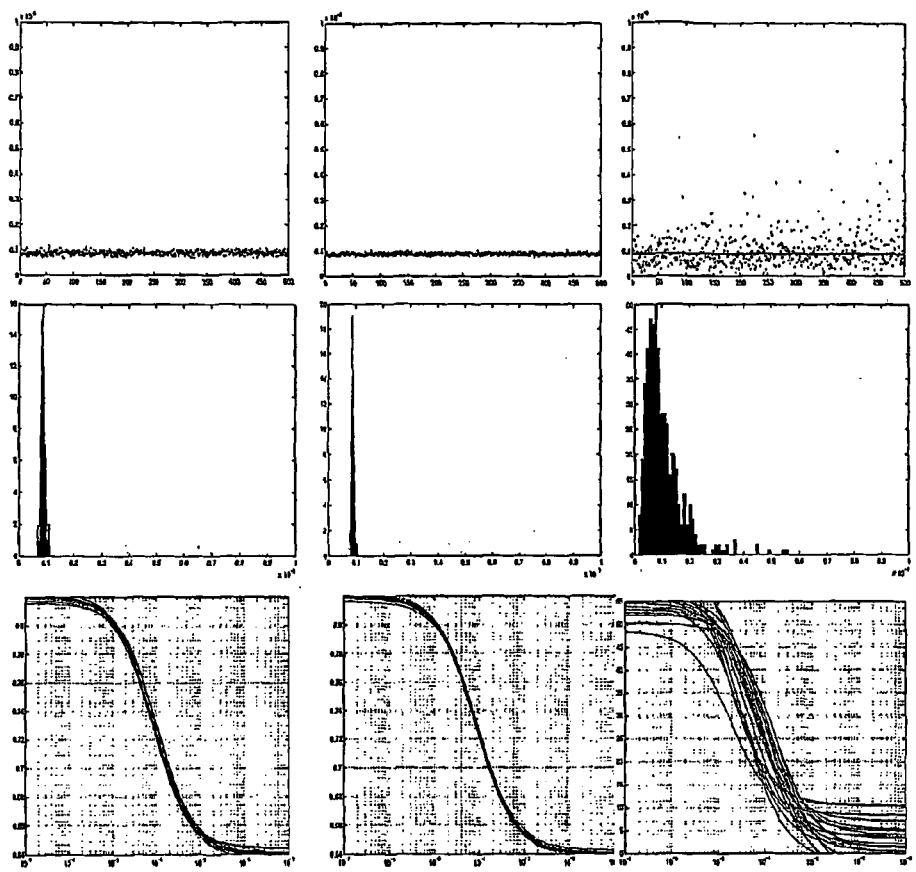
FIG. 17 is a family of plots showing a best-case response for well-well mean FLIN response.

Monte Carlo Response Curve Estimates: To quantify the effect of measurement precision directly on estimated inhibitor response parameters, a Monte Carlo simulation was carried out using the model response shown in FIG. 15 which shows a theoretical dose response curve with $IC_{50}=8.895\times 10^{-5}$, and $\mu_{max}$, $\mu_{min}$ and $\sigma$ specified by the measurement procedure to be simulated. For FIG. 15, $\mu_{max}=1.0$, and $\mu_{min}=0.0$. The circled points indicate the 11 inhibitor concentrations used in the simulation. These eleven sites were chosen logarithmically across the inhibitor concentration range to which Gaussian random noise with deviation $\sigma/\sqrt{n}$ was added to create 500 simulated experimental outcomes. FIGS. 16 and 17 illustrate the simulated datasets, each nonlinearly regressed to the model in FIG. 15 using the Gauss-Newton procedure [See, for example, W H Press, S A Teukolsky, W T Vetterling, and B P Flannery. *Numerical Recipes in C, Second Edition*. Cambridge University Press, New York, N.Y., 1992.].

The panels of FIG. 16 comparatively illustrate worst case simulated dose response experiments achieved by way of empirical curve $IC_{50}$ distribution for well-well mean FLIN response. The top three panels show estimated $IC_{50}$ scatterplots with true value. The middle three panels are $IC_{50}$ frequency histograms (compare with the 5 and 95-percentile values in Table 7). The bottom panels illustrate a sample of 20 estimated dose response curves from the total simulation of 500. The leftmost three panels show a 90% $IC_{50}$ confidence interval in the worst case for our invention with full population, with σ=0.093. However, our worst case is approximately 3.62× better (narrower) than the rightmost three panels (Ding et al.). Results for our $G_1$ subpopulation (center; worst case σ=0.066) exploit the homogeneity of this subpopulation to give a 90% $IC_{50}$ confidence interval that is 5.07× better. Experimental parameters for the simulation are given in Table 7.

cally plotted for the invention (middle column; σ=0.0665, Δμ=0.18), and Ding et al. (right column; σ=83.545, Δμ=56).

Figure 19:
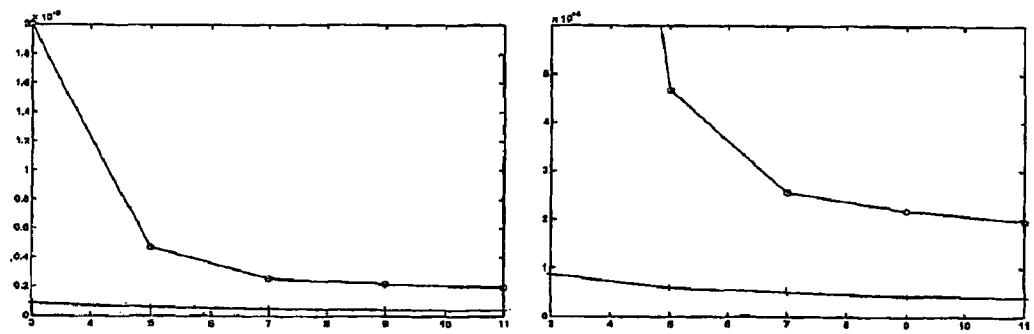
FIG. 19 includes curves that show Monte Carlo confidence interval width versus sample concentrations.

Refer further to FIG. 19, which shows $IC_{50}$ Monte Carlo confidence interval width for Ding et al. (circles; σ=83.545, Δμ=56) and the invention (plusses; σ=0.0665, Δμ=0.18) versus number of sample concentrations (3,5,7,9,11). The right-hand curve of FIG. 19 is a zoom of the left-hand curve. Manifestly, 10 measurement precision becomes more important as sampling and coverage of the relevant concentration ranges decreases. The elbow in the graph corresponds to a regression breakdown, showing robust regression results maintained by the measurement precision of the invention.

TABLE 7

Monte Carlo simulated dose response parameters and estimation results for 500 runs at n = 100 cellular measurements, showing $\Delta IC_{50}$ 90% Monte Carlo confidence interval variability under different measurement precisions. Well-to-well mean FLIN response standard errors: 0.0093 (invention; worst case full cellular population), 0.0040 (invention; best case full cellular population), 0.0066 (invention; worst case $G_1$ subpopulation), 0.0021 (invention; best case $G_1$ subpopulation), and 8.3545 (Ding et al.).

| std dev | range | CV | $IC_{50}$ 5% | $IC_{50}$ 95% | $\Delta IC_{50}$ |
|---|---|---|---|---|---|
| 0.093 | [.15, .33] | 51% | $6.2930 \times 10^{-5}$ | $1.2151 \times 10^{-4}$ | $5.8585 \times 10^{-5}$ |
| 0.040 | [.15, .33] | 22.2% | $7.8407 \times 10^{-5}$ | $1.0247 \times 10^{-4}$ | $2.4063 \times 10^{-5}$ |
| 0.066 | [.15, .33] | 35.1% | $7.0982 \times 10^{-5}$ | $1.1109 \times 10^{-4}$ | $4.1808 \times 10^{-5}$ |
| 0.021 | [.15, .33] | 11.7% | $8.2296 \times 10^{-5}$ | $9.5332 \times 10^{-5}$ | $1.3036 \times 10^{-5}$ |
| 83.545 | [0, 55] | 152% | $3.3819 \times 10^{-5}$ | $2.4584 \times 10^{-4}$ | $2.1202 \times 10^{-4}$ |

In FIG. 17 best case simulated dose response experiments illustrate empirical curve $IC_{50}$ distribution for well-well mean FLIN response. Shown are estimated $IC_{50}$ scatterplots with true value (the top three panels), $IC_{50}$ frequency histograms (the middle three panels; compare with 5 and 95-percentile values in Table 7); and a sample of 20 estimated dose response curves from the total simulation of 500 (in the bottom three panels). The 90% $IC_{50}$ confidence interval for the left hand side (simulation of results produced by the invention; best case full population, σ=0.040) is approximately 8.81× better (narrower) than the right (simulation of results produced according to Ding et al.). Results for the invention's $G_1$ subpopulation (center, best case, σ=0.021) exploit the homogeneity of this subpopulation to give a 90% $IC_{50}$ confidence interval that is 16.3× better. Experimental parameters for the simulation are given in Table 7.

Standard errors for response point estimates were 0.0093 (worst case Table 4 standard deviation), 0.004 (best case Table 4 standard deviation) and 8.354 (calculated from the cell numbers for statistical significance reported in Ding et al. and replicated in Table 6); both standard errors assume n=100. Table 7 reports the 90% Monte Carlo confidence interval widths for all three outcomes, $5.8585 \times 10^{-5}$, $2.4063 \times 10^{-5}$ and $2.1202 \times 10^{-4}$, showing 3.62× (worst case) and 8.81× (best case) stronger confidence in the $IC_{50}$ estimates obtained for our invention. Further simulations shown in FIGS. 18 and 19 demonstrate the sensitivity of $IC_{50}$ estimate precision on the sampling of experimental concentrations.

Figure 18:
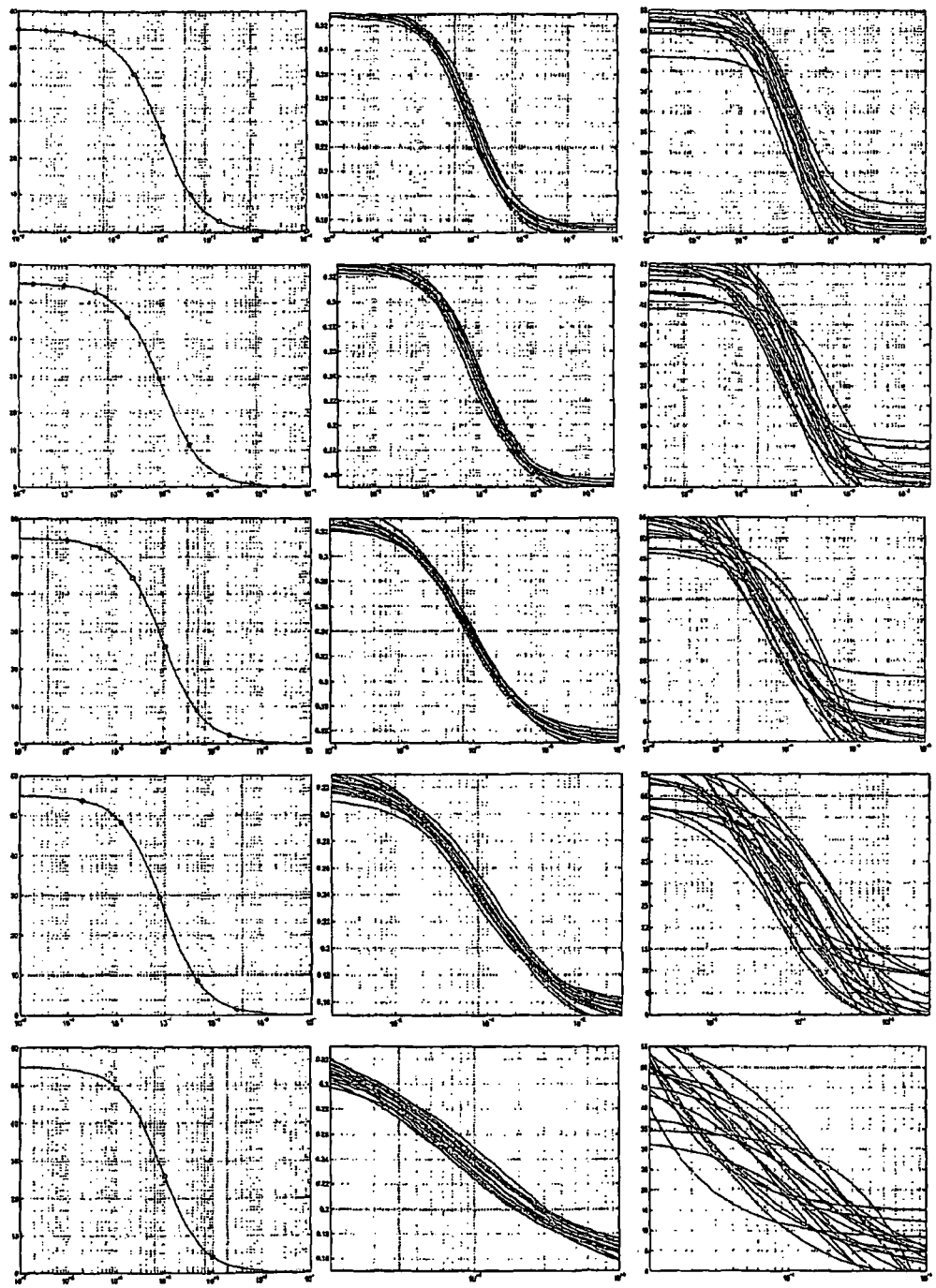
FIG. 18 is a family of plots showing the results of a Monte Carlo simulation of dose response regression.

For example, in FIG. 18, Monte Carlo simulations of dose response regression reveal that $IC_{50}$ estimates becomes more sensitive to cell-measurement precision as the range of experimental concentrations diminishes. The panels in the left column show the model sigmoids used in the experiments, ranging from 11 concentrations (top; circles) to 3 concentrations (bottom; circles). 20 of 500 runs are graphi- Homogeneous Sub Ovulation Analysis To illustrate the ability of the invention to estimate quantities of interest conditionally on specific morphologic subpopulations, an empirically determined classification scheme was developed to isolate $G_1$ cells from the S, M, $G_2$ cells and fluorescent artifacts. A six-rule classifier (Table 9) was developed from the set of standard cellular measurements (Table 8) taken in the Hoechst 33342 or DAPI nuclear channel. Analysis of translocation experiment data was repeated for this $G_1$ subpopulation at 2500 cells/well (rows D,E) and is reported in Tables 10 (raw well data), 11 (statistics of well means) and FIG. 20 in which the translocation response of the $G_1$ subpopulation is plotted. The row aggregate (average of all well average subpopulation FLIN responses) are 0.1418 (unstimulated) and 0.3317 (stimulated).

Figure 20:
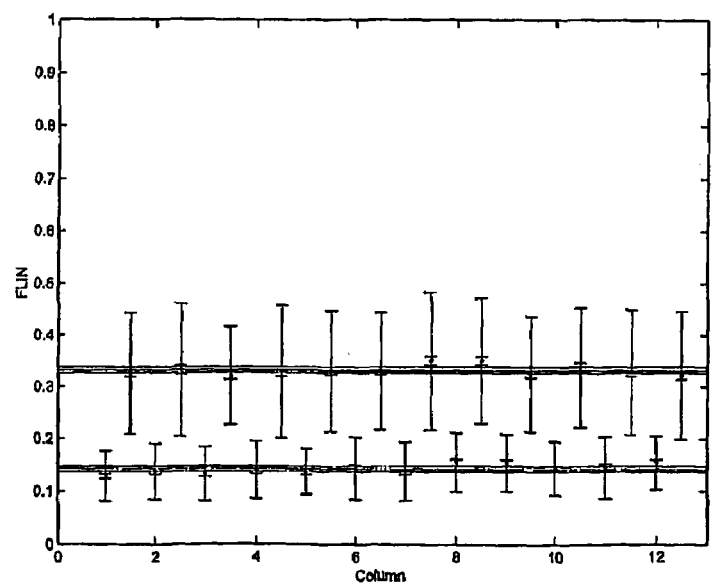
FIG. 20 is a plot showing a translocation response of the $G_1$ subpopulation according to the invention.

The improved homogeneity of cell response is clearly seen in reduced ±2σ population intervals (compare FIG. 13, middle, with FIG. 20). The subpopulation defined by Table 9 responds about twice as uniformly as the full cellular population, while the mean response is nearly identical. Well-to-well variability appears consistent with the full population analysis.

Table 12 reports sample size requirements for the NFκB translocation experiment assuming measurements are restricted to the $G_1$ subpopulation. The improvement over the full population requirements at 20% response resolution (giving the minimum of 5 samples used in a dose response regression), is 42 cells to <30 cells (29% reduction) at α=0.05, β=0.20; 68 to <30 (56% reduction) at α=0.01, β=0.20; and 256 to 47 (82% reduction) at α=0.001, β=0.001. The subpopulation analysis reduced cell number requirements by the 94% over data reported by Ding et al. (α=0.05 and 0.01 for 20% response case).

The Monte Carlo simulations were also repeated using the $G_1$ subpopulation statistics. Experimental parameters and numerical $IC_{50}$ 90% confidence interval widths given in Table 7 show a 28.6% -45.8% reduction in interval width over full population analysis for the same number of cells n=100. Comparison to the simulations based on Ding et al. (as described above) show a 5.07-fold improvement in the worst case, visualized in FIG. 16 (compare middle and right columns), and a 16.3-fold improvement in the best case, visualized in FIG. 17.

These results indicate that improved response can be exploited by reducing the required scan area and keeping a specified resolution (optimizing for system throughput), or fixing the scan area and thus throughput, but discarding cellular measurements in an intelligent manner to select homogenous response populations and improving response resolution. These advantages will only be available when the fraction of cells that define the subpopulation exceeds a threshold defined by the response resolution equations. For example, a scan area can be reduced from the minimum required to measure the fill population $n_F$ whenever $$n_s < n_{Ff} \text{ or } \frac{n_s}{n_F} = \frac{\sigma_s^2}{\sigma_F^2} < f \quad (17)$$

where f is the fraction of cells comprising the homogenous subpopulation. When this is true, the scan area can be reduced by some number of fields dependent on cellular density and f. Thus, subpopulation analysis can directly affect system throughput whenever a homogenous enough and large enough subpopulation exists. Similarly, minimum significant response is improved whenever $$MSR_S - MSR_F > 0 \text{ or } \sigma_S - \sigma_F \sqrt{f} > 0 \quad (18)$$

These rules can be validated by examining the curves in FIG. 14.

TABLE 8

Standard cellular measurements

| measurement | definition |
| --- | --- |
| 1 serial number | i |
| 2 x coordinate of nuclear bounding box center | $x_b$ |
| 3 y coordinate of nuclear bounding box center | $y_b$ |
| 4 x size of nuclear bounding box | $\Delta x_b$ |
| 5 y size of nuclear bounding box | $\Delta y_b$ |
| 6 nuclear area | $a_n$ = #nuclear pixels |
| 7 root nuclear area | |
| 8 integrated nuclear intensity | $I_a = \Sigma_n I(x, y)$ |
| 9 average nuclear intensity | $\bar{I}_n = I_n/a_n$ |
| 10 minimum nuclear intensity | $p_0 = \min[I_n(x, y)]$ |
| 11 5th percentile of nuclear intensity | $p_5 = 5\%[I_n(x, y)]$ |
| 12 25th percentile of nuclear intensity | $p_{25} = 25\%[I_n(x, y)]$ |
| 13 50th percentile of nuclear intensity | $p_{50} = 50\%[I_n(x, y)]$ |
| 14 75th percentile of nuclear intensity | $p_{75} = 75\%[I_n(x, y)]$ |
| 15 95th percentile of nuclear intensity | $p_{95} = 95\%[I_n(x, y)]$ |
| 16 maximum nuclear intensity | $p_{100} = \max[I_n(x, y)]$ |
| 17 interquartile range of nuclear intensity | $IQ_n = p_{75} - p_{25}$ |
| 18 variance of nuclear intensity | |
| 19 standard deviation of nuclear intensity | $\sigma_n$ |
| 20 third central moment of nuclear intensity | $m_{n,3} = (a_n - 1)^{-4} \Sigma_n (I(x, y) - I_n)^3$ |
| 21 $3^{rd}$ root of $3^{rd}$ central moment of nuclear intensity | $m_{n,3}^{1/3}$ |
| 22 fourth central moment of nuclear intensity | $m_{n,4} = (a_n - 1)^{-4} \Sigma_n (I(x, y) - I_n)^1$ |
| 23 $4^{th}$ root of $4^{th}$ central moment of nuclear intensity | $m_{n,4}^{1/4}$ |
| 24 nuclear perimeter | $I_n$ = #nuclear pixels (8-connected) |
| 25 nuclear wiggle | $w = I_n/a_n$ |
| 26 normalized nuclear wiggle | $\bar{I}p = I_n/\sqrt{a_n}$ |
| 27 channel-j integrated intensity | $I_j = \Sigma I_j(x, y)$ |
| 28 channel-j integrated nuclear intensity | $I_{a,j} = \Sigma_n I_j(x, y)$ |
| 29 channel-j integrated cytoplasmic intensity | $I_{a,j} = \Sigma_n I_j(x, y)$ |
| 30 channel-j FLIN | $I_{a,j}/(I_{a,j} + I_{n,j})$ |

TABLE 9

Six-rule definition for $G_1$ subpopulation based on cellular measurements defined in Table 8

| rule | effect (property of cells excluded) |
| --- | --- |
| 1 $22.73 \leq \sqrt{a_n} \leq 31.85$ | nuclear area is atypical of resting cell nuclei |
| 2 $10^5 \leq I_j \leq 4 \times 10^5$ | little or no NFκB fluorophore or large, bright fluorescent artifacts |
| 3 $m_{n,3} < 0$ | dividing, have unusual nuclear shapes or are dying |
| 4 $.11 \leq w \leq .2$ | two or more aggregate nuclei or irregularly shaped nuclei |
| 5 $10 \leq IQ_n \leq 60$ | irregular nuclear textures |
| 6 $-w < 4.8$ | irregularly shaped nuclei |

TABLE 10

Well-wise and row-pooled FLIN statistics of $G_1$ subpopulation, as defined by the classifier in Tables 8 and 9. CVs defined as (std dev)/mean. These results show significant reduction in cell response variability, indicating a much more homogenously responding subpopulation amongst the total cell population in each well. See FIG. 20 for a visualization of this data.

| Well | n | mean | std dev | std err | CV |
| --- | --- | --- | --- | --- | --- |
| D1 | 53 | 0.139494 | 0.026964 | 0.003704 | 0.193301 |
| D2 | 79 | 0.135942 | 0.021481 | 0.002417 | 0.158018 |
| D3 | 85 | 0.142980 | 0.029554 | 0.003206 | 0.206699 |
| D4 | 128 | 0.137386 | 0.027846 | 0.002461 | 0.202687 |
| D5 | 70 | 0.154410 | 0.027970 | 0.003343 | 0.181141 |
| D6 | 75 | 0.153748 | 0.027003 | 0.003118 | 0.175630 |
| D7 | 88 | 0.142782 | 0.025264 | 0.002693 | 0.176942 |
| D8 | 102 | 0.145129 | 0.029421 | 0.002913 | 0.202720 |
| D9 | 72 | 0.153787 | 0.025640 | 0.003022 | 0.166723 |
| D10 | 114 | 0.127378 | 0.023832 | 0.002232 | 0.187094 |
| D11 | 106 | 0.136946 | 0.026416 | 0.002566 | 0.192890 |
| D12 | 107 | 0.131305 | 0.025726 | 0.002487 | 0.195925 |

TABLE 10-continued

Well-wise and row-pooled FLIN statistics of $G_1$ subpopulation, as defined by the classifier in Tables 8 and 9. CVs defined as (std dev)/mean. These results show significant reduction in cell response variability, indicating a much more homogenously responding subpopulation amongst the total cell population in each well. See FIG. 20 for a visualization of this data.

| Well  | n    | mean     | std dev  | std err  | CV       |
|-------|------|----------|----------|----------|----------|
| Row D | 1029 | 0.1406   | 0.0277   | 0.0008   | 0.1969   |
| E1    | 204  | 0.328162 | 0.064145 | 0.004491 | 0.195469 |
| E2    | 236  | 0.330019 | 0.058368 | 0.003799 | 0.176861 |
| E3    | 257  | 0.329866 | 0.056664 | 0.003535 | 0.171778 |
| E4    | 230  | 0.350588 | 0.066655 | 0.004395 | 0.190124 |
| E5    | 269  | 0.349991 | 0.060755 | 0.003704 | 0.173590 |
| E6    | 255  | 0.324779 | 0.055980 | 0.003506 | 0.172363 |
| E7    | 241  | 0.337747 | 0.058013 | 0.003737 | 0.171766 |
| E8    | 227  | 0.327979 | 0.060758 | 0.004033 | 0.185250 |
| E9    | 290  | 0.322116 | 0.061913 | 0.003636 | 0.192207 |
| E10   | 278  | 0.325874 | 0.058762 | 0.003524 | 0.180322 |
| E11   | 204  | 0.331738 | 0.064243 | 0.004498 | 0.193656 |
| E12   | 162  | 0.320942 | 0.047253 | 0.003713 | 0.147232 |
| Row E | 2853 | 0.3318   | 0.0606   | 0.0011   | 0.1821   |

TABLE 11

Well-well statistics of well subpopulation average FLIN (n = 12), as defined by the classifier in Tables 8 and 9. Mean, standard deviation, standard error and coefficient of variation of the FLIN well sample means across each row. Although standard error is increased due to the reduced number of participating cells in the subpopulation average, well-well variability is consistent with the full population data reported in Table 5. See FIG. 20 for a visualization of this data.

| Row | mean   | std dev | std err | CV     |
|-----|--------|---------|---------|--------|
| D   | 0.1418 | 0.0088  | 0.0026  | 0.0624 |
| E   | 0.3317 | 0.0097  | 0.0028  | 0.0295 |

TABLE 12

Minimum number of $G_1$ subpopulation cells required to resolve percent of the total NFκB translocation at maximum stimulation, reported here and in [6], at controlled error probabilities (type I, type II). Our calculations assume $\Delta\mu = 0.1818$ and $\sigma$ linearly interpolated between 0.0267 (unstimulated) and 0.0542 (stimulated). See Table 6 caption for additional assumptions.

| % Maximum Response | Ding et al. (0.05, 0.20) | Invention (0.05, 0.20) | Ding et al. (0.01, 0.20) | Invention (0.01, 0.20) | Invention (0.001, 0.001) |
|---|---|---|---|---|---|
| 2%   | Not given | 624 | Not given | 1013 | 3855 |
| 5%   | Not given | 103 | Not given | 168  | 637  |
| 10%  | Not given | <30 | Not given | 44   | 168  |
| 20%  | >500      | <30 | >500      | <30  | 47   |
| 30%  | 388       | <30 | >500      | <30  | <30  |
| 35%  | 220       | <30 | 331       | <30  | <30  |
| 45%  | 141       | <30 | 213       | <30  | <30  |
| 55%  | 99        | <30 | 149       | <30  | <30  |
| 65%  | 73        | <30 | 111       | <30  | <30  |
| 70%  | 57        | <30 | 86        | <30  | <30  |
| 80%  | 45        | <30 | 68        | <30  | <30  |
| 90%  | 37        | <30 | 56        | <30  | <30  |
| 100% | 31        | <30 | 47        | <30  | <30  |

FIGS. 21a and 21b illustrate inhibition of NFκB nuclear translocation by BIPI compound A. In these figures, Fractional Localized Intensity in the Nucleus (FLIN) is plotted versus inhibitor concentration for full cell population found in the 10×10-field scan area (FIG. 21a), and in a 100-cell population (FIG. 21b). Cell preparation is as described above. FIG. 21a illustrates total cell population analysis with inhibition of NFκB nuclear translocation in HUVEC cells where Ki(Cmpd_A)=6.95E−05, Rmax=3.86E−01, and Rmin=0.212. FIG. 21b illustrates 100-cell population analysis with inhibition of NFκB nuclear translocation in HUVEC cells where Ki(Cmpd_A)=8.09E−05, Rmax=4.21E−01, and Rmin=0.212.

FIGS. 22a and 22b illustrate inhibition of NFκB nuclear translocation by BIPI compound B. In these figures, Fractional Localized Intensity in the Nucleus (FLIN) is plotted versus inhibitor concentration for full cell population found in the 10×10-field scan area (FIG. 22a), and in a 100-cell population FIG. 22b). Cell preparation is as described above. FIG. 22a illustrates total cell population analysis with inhibition of NFκB nuclear translocation in HUVEC cells where Ki(Cmpd_B=5.08E−05, Rmax=3.77E−01, and Rmin=0.212. FIG. 22b illustrates 100-Cell population analysis with inhibition of NFκB nuclear translocation in HUVEC cells where Ki(Cmpd_B)=6.65E−05, Rmax=4.12E−01, and Rmin=0.212. FIGS. 23a and 23b illustrate inhibition of NFκB nuclear translocation by BIPI compound C. Fractional Localized Intensity in the Nucleus (FLIN) is plotted versus inhibitor concentration for full cell population found in the 10×10-field scan area (FIG. 23a), and in a 100-cell population (FIG. 23b). Cell preparation is as described above. FIG. 23a illustrates total cell population analysis with inhibition of NFκB nuclear translocation in HUVEC cells where Ki(Cmpd_C=1.01E−06, Rmax=3.99E−01, and Rmin=0.212E−01. FIG. 23b illustrates 100-ell population analysis with inhibition of NFκB nuclear translocation in HUVEC cells where Ki(Cmpd_C)=1.36E−06, Rmax=4.20E−01, and Rmin=0.212.

Figure 24:
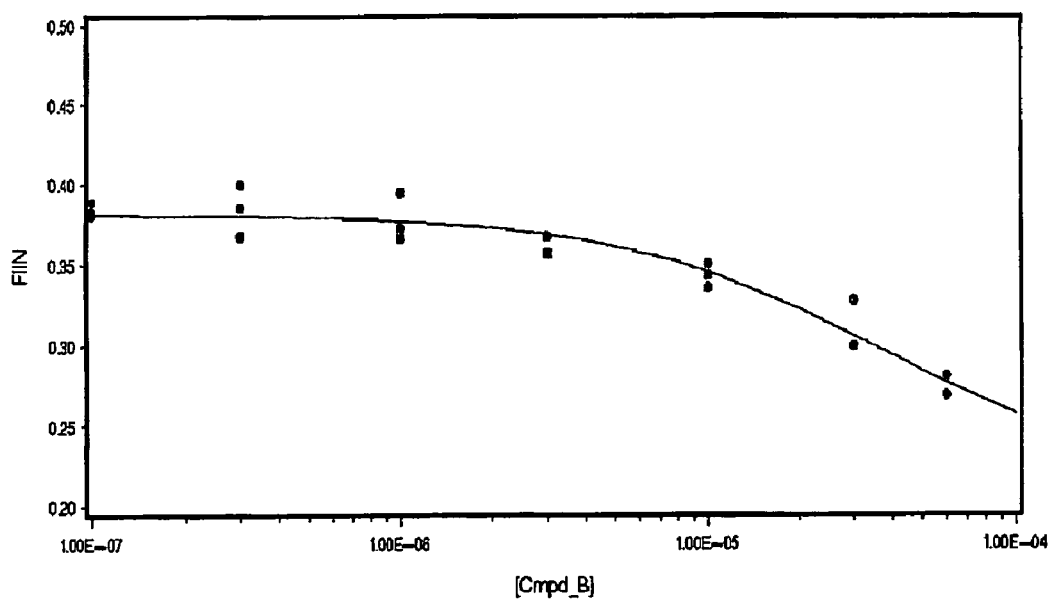
FIG. 24 illustrates inhibition of NFκB nuclear translocation by BIPI compound B in a defined $G_1$ cell subpopulation

FIG. 24 illustrates inhibition of NFκB nuclear translocation by BIPI compound B in the $G_1$ cell subpopulation defined by Tables 8 and 9 with Fractional Localized Intensity in the Nucleus (FLIN) plotted versus inhibitor concentration for full cell population found in the 10×10-field scan area. Cell preparation is as described above. In this figure, G1 cell population analysis is shown with inhibition of NFκB nuclear translocation in HUVEC cells where Ki(Cmpd_B)=3.70E−05, Rmax=3.82E−01, and Rmin=0.212.

TABLE 13

Inhibitor response parameter estimates and standard errors, given by nonlinear regression analysis. Unity-slope-at-inflection sigmoid models were fit to triplicate wells at seven concentrations to determine the response characteristics for BIPI inhibitor compounds A, B and C. Each compound was evaluated using the full population of cellular measurements found in a 10 × 10-field scan area within each well, and also limiting the number of cells measured to 100 in each well. $R_{min}$ could not be established independently in compounds A, B (see FIGS. 21a/21b and 23a/23b), and so $R_{min}$ was fixed at 0.212 for these compounds (all compounds with fixed $R_{min}$ marked with asterisks), as determined by the full population analysis of compound C. The $G_1$ subpopulation response was also measured for compound B. Cells were prepared as described above.

| Compound | $R_{max}$ (FLIN) (SE) | $R_{min}$ (FLIN) (SE) | $IC_{50}$ (FLIN) (SE) |
|---|---|---|---|
| A | 0.386 (8.17 × 10$^{-3}$) | 0.212* | 6.95 × 10$^{-5}$ (2.2 × 10$^{-5}$) |
| A (n = 100) | 0.421 (6.70 × 10$^{-3}$) | 0.212* | 8.09 × 10$^{-5}$ (1.8 × 10$^{-5}$) |
| B | 0.377 (3.63 × 10$^{-3}$) | 0.212* | 5.08 × 10$^{-5}$ (6.8 × 10$^{-6}$) |
| B (n = 100) | 0.412 (5.85 × 10$^{-3}$) | 0.212* | 6.65 × 10$^{-5}$ (1.3 × 10$^{-5}$) |
| B ($G_1$) | 0.382 (3.28 × 10$^{-3}$) | 0.212* | 3.70 × 10$^{-5}$ (4.1 × 10$^{-6}$) |
| C | 0.399 (6.90 × 10$^{-3}$) | 0.212 (3.78 × 10$^{-3}$) | 1.02 × 10$^{-6}$ (1.6 × 10$^{-7}$) |
| C (n = 100) | 0.424 (8.96 × 10$^{-3}$) | 0.212* | 1.15 × 10$^{-6}$ (2.2 × 10$^{-7}$) |

Analysis of Inhibitor Compounds: In another wellplate, cells were treated with different concentrations of three inhibitor compounds (A,B and C), and then analyzed to assess the inhibition of NFAB translocation. In these experiments, both the full number of cells found in a 10×10 scan area, and a fixed 100 cell set were measured and compared. All three compounds responded clearly (FIGS. 21*a*-23*b*), with nearly identical uninhibited translocation ($R_{max}$) in the range 0.3772-0.4239. Compounds A and B failed to plateau at maximum inhibitor concentration, and response estimates failed to converge with a floating $R_{min}$ parameter. Compound C achieved maximum inhibition with $R_{min}$=0.212 (full cell population) and 0.220 (100 cell population); $R_{min}$ was subsequently fixed to achieve response convergence on compounds A and B. Table 13 summarizes all estimated response parameters calculated by nonlinear optimization (unity slope at inflection is assumed in the response model). $IC_{50}$s varied 1.02×10$^{-6}$-1.15×10$^{-6}$ for compound C, and by a factor in the approximate range 32-80 greater for compounds A and B.

TABLE 14

Scan rate timing model components with definitions and estimated default values.

| timing component | time required to | estimated value |
|---|---|---|
| $t_{plate, M \times N}$ | scan a M × N plate | see equation |
| $t_{well, Q \times R}$ | scan a Q × R field area inside a well | see equation |
| $t_{field}$ | image a single field | see equation |
| $t_{I,k}$ | integrate the $k^{th}$ image channel | ≥0.0167 s |
| $t_{MW}$ | move between adjacent wells and setup scan | 1.00 s |
| $t_{MF}$ | move between adjacent fields | 0.30 s |
| $t_{RW}$ | return from end of field row inside a well | 0.50 s |
| $t_F$ | focus on a single field | 0.40 s |
| $t_T$ | transfer image data from camera | 0.11 s |
| $t_E$ | reconfigure emission/excitation filters | 0.20 s |
| $t_S$ | open/close shutter | 0.03 s |
| $t_C$ | adjust camera parameters | 0.10 s |

TABLE 15

System timing examples showing typical system throughput dependence on assay and cell preparation protocol, assuming two channel scans, 3 × 3 well scan areas, 96 well plates and estimated component times listed in Table 14. A bright fluorescent intensity ($t_{I,2}$ = 0.0167 s) requires 0.9834 s/well and 20.22 m/plate, while a dimmer fluorescent intensity ($t_{I,2}$ = 0.5000 s), perhaps due to fluorophore binding to a less concentrated target, requires 16.0 s/well and 27.18 m/plate. Both secondary channels assume a bright nuclear fluorophore as the primary channel ($t_{I,1}$ = 0.0167 s). Sufficient online image processing power is assumed available so that throughput is scan-hardware limited.

| $t_{I,2}$ | $t_{field}$ | $t_{well,3 \times 3}$ | $t_{plate,8 \times 12}$ |
|---|---|---|---|
| 0.0167 s | 0.9834 s | 11.65 s | 20.22 m |
| 0.5000 s | 1.4667 s | 16.0 s | 27.18 m |

Scan Rate Estimates: A simple model of scan rates is broken into plate, well and field components $$t_{plate, M \times N} = MNt_{well, Q \times R} + (MN - 1)t_{MW} \qquad (19)$$

$$t_{well, Q \times R} = QRt_{field} + Q(R - 1)t_{MF} + (Q - 1)t_{RW} \qquad (20)$$

$$t_{field} = t_S + t_F + \sum_{k=1}^{n} t_{I,k} + nt_T + (n - 1)(t_E + t_C) \qquad (21)$$

with definitions and estimated values given in Table 14. The assumptions in this model include: (1) wellplates are scanned in a zigzag pattern, (2) wells are scanned, in a raster pattern requiring a return between rows to maximize field alignment, (3) online processing occurs completely in the background so that system is scan-hardware limited.

Table 15 gives timing example estimates for scanning a 2-channel, 96 wellplate with 3×3 well scan areas for the two cases of a bright and dim (requiring integration) secondary channel (examples both assume a bright primary nuclear channel), resulting in 11.65 s/well, 20.22 m/plate for the bright assay, and 16.0 s/well, 27.18 m/plate for the dim assay. These examples are not specific to a particular application, which may require more or less time depending on parameters, but are intended to suggest the scope of scan rates that will be typical for assays developed for the platform of FIG. 1.

When comparing scan rates for the platform of FIG. 1 with other imaging platforms, $t_F$ and Q×R are the dominant factors. We found that $t_F$=0.4 s was achieved due to the speed of the autofocus technology described above. The well scan area Q×R is chosen to allow imaging of a sample size large enough to accommodate some minimum significant response. Since a required minimum significant response (MSR) fixes n, we can define the ratio of the required field acquisition times of two systems or assays as the time efficiency (TE) for comparison $$TE(MSR) = \frac{n_A(MSR)d_B t_{field,A}}{n_B(MSR)d_A t_{field,B}} \qquad (22)$$

where A, B are comparable systems and d is the cellular field density (cells/field). TE accounts for differences in number of cells necessary between systems, but for simplicity, neglects times related to stage motion.

Figure 25:
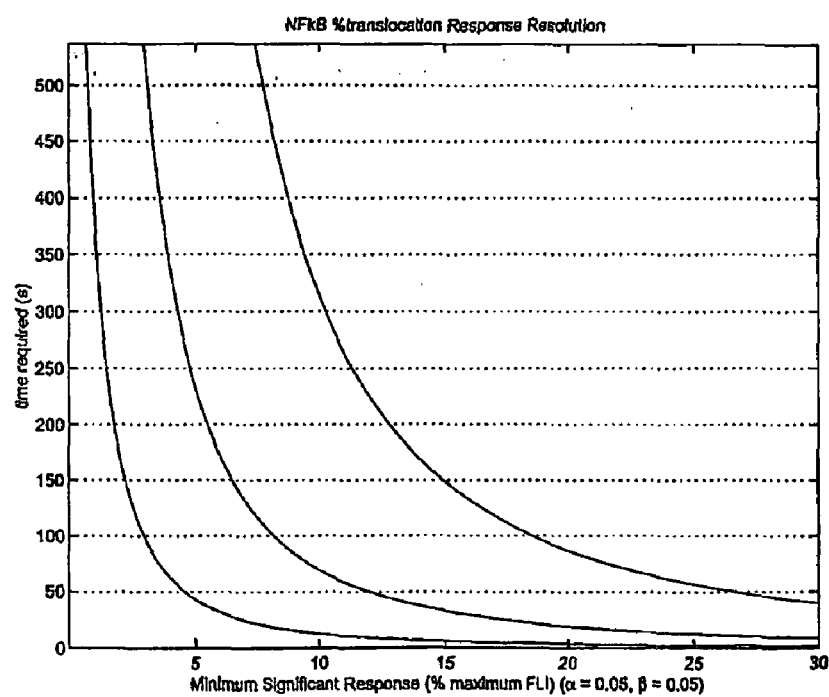
FIG. 25 is a family of curves produced by plotting time required to achieve a minimum significant response as a percent of total NFκB translocation on maximum stimulation per well.

Comparing the systems from Table 6 for NFκB translocation (B is the platform of FIG. 1) at α=0.05, β=0.20, $d_B/d_A$=0.25, MSR=20% and letting $t_{field,A}/t_{field,B}$ vary between 2-6 gives a TE range of 5.95-17.85. Although this efficiency comparison relates strictly to NFκB translocation assays as reported here and in Ding et al., the range illustrates fundamental advantages over the platform described in Ding et al. afforded by the autofocus and image segmentation speed, and in image measurement fidelity that will manifest in other assays (specific TEs would have to be calculated for each). The high end of the TE range here would become possible, for example, if the protocol were optimized for the platform of FIG. 1 to brighten the secondary channel, thereby taking better advantage of the autofocus speed. Scan rate comparisons between NFκB assays can also be cast into an absolute time scale by additionally assuming specific cells/field densities. FIG. 25 shows time (seconds) versus MSR (percent of total translocation dynamic range) curves for both the platform of FIG. 1 and the platform used by Ding et al., under typical experimental conditions.

FIG. 25 is a family of curves produced by plotting time required to achieve a minimum significant response ((MSR) as a percent of total NFκB translocation on maximum stimulation) per well. In these curves (lowest to highest), $\sigma=0.040$, best case for the platform of FIG. 1; $\sigma=0.093$, worst case for the platform of FIG. 1; $\sigma=0.277=2.98\times0.093$, the platform of Ding et al., 2.98=ratio of measurement CVs (see Table 7). Assumptions: $\alpha=\beta=0.05$, $t_{field,Dingetal}=3$ s, $t_{field,figure1platform}=1.4667$ s, $d_{Dingetal}=40$ cells/field (10× objective magnification), $d_{figure1platform}=10$ cells/field (20× objective magnification).

An Automatic Tool for Achieving Minimum Significant Response in a Drug Screen: The error measurements described above can be used to predict the number of cells needed to reach a required minimum significant response for in a given compound screen. A graphical user interface tool will lead the user through the steps of measuring control and test wells to determine the errors. This predictor tool will allow the user to manipulate the time required to scan a plate as a function of the minimum significant response for the cell population and/or subpopulation. With this automation, the use can easily determine whether or not to use a subpopulation or the full population and how much time will be required to reach a given significance. The scan will then proceed automatically by scanning each well until the required number of cells is measured.

Refer now to FIGS. 26a, 26b, 27, 28, and 29 for an understanding of a method of performing an automated drug screen according to the invention. These figures include screens of a graphical user interface (GUI) designed to afford a user the ability to select and set parameters to perform the automated drug screen using the principles and functions of this invention; they also include flow charts representing initialization and performance of a drug screen according to the invention. The illustrated method represents functionality invested in the high throughput platform illustrated in FIG. 1 by programming the host computer 110 with a series of software instructions. It may also be said that these figures illustrate a method performable by a programmed computer. The GUI screens represent visible output produced on the monitor 115; they also represent functionality for identifying to a user parameters of a drug screen, and for enabling the user to input values for those parameters to the host computer 110. These screens may also be referred to as "GUI tools".

Figure 28:
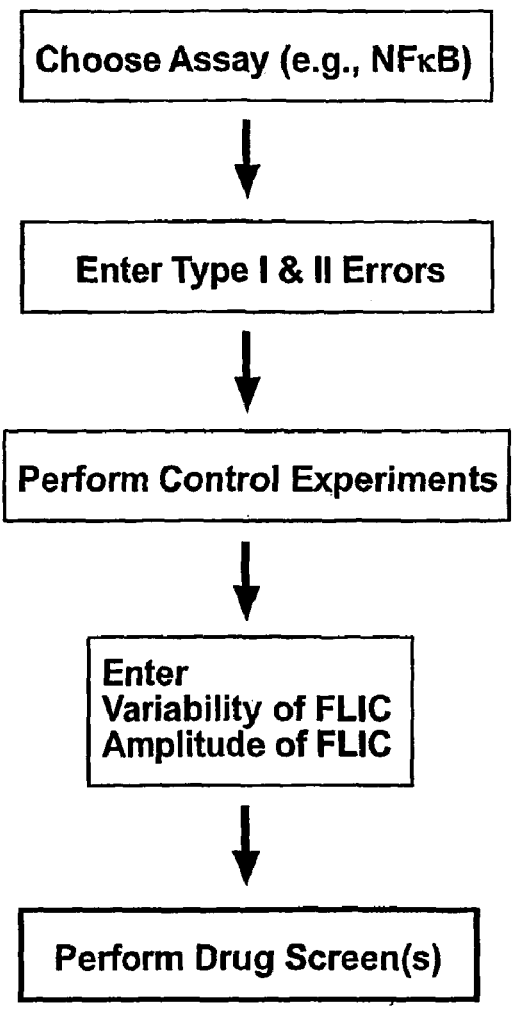
FIG. 28 is a flow diagram representing steps executed in initializing a drug screen.

Referring now to these figures, FIGS. 26a, 26b, and 28 show user-executed steps carried out prior to performing the automated drug screen in order to initialize parameters that control the screen. The user first chooses an assay that may be run for many days or weeks. NF☐B is an example of such an assay. The Type I and Type II errors (equations 8-16) are then entered into the host computer 110 through a GUI tool shown in FIG. 26a. Control experiments are then performed to measure the variability and amplitude of FLIC. When these values are at hand, they are entered into the host computer 110 through a GUI tool shown in FIG. 26b. The variability is the standard deviation (SD) or coefficient of variation (CV) of FLIC and the percent amplitude is computed as 100×(maximum-minimum)/(instrument measurement range). The maximum and minimum are determined by the cellular responses to controls (usually with no compound and with a maximally stimulating compound).

Figure 29:
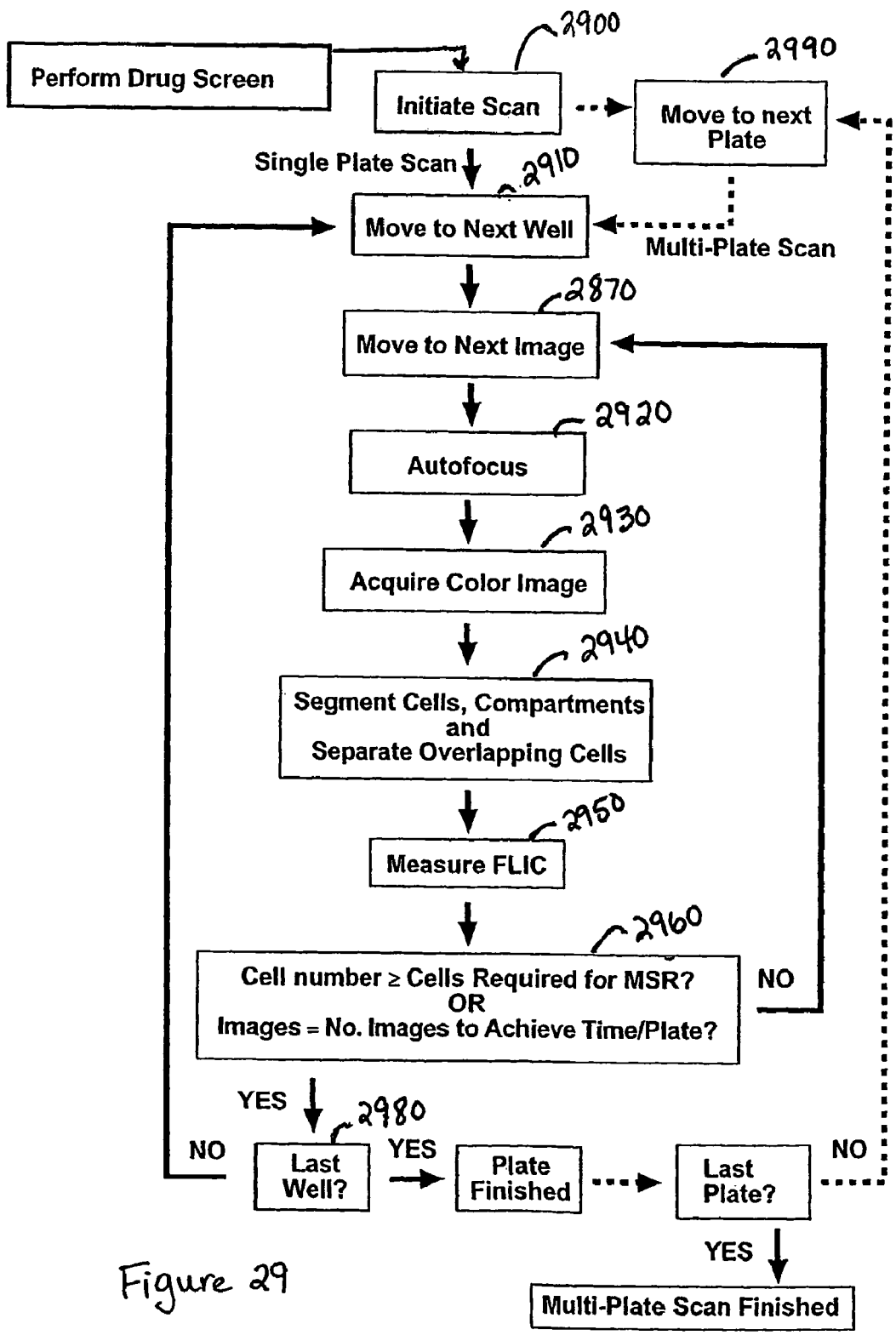
FIG. 29 is a flow diagram representing a drug screen method performed by a programmed computer according to this invention and also representing a software program for causing the method to be performed.

The automated drug screen is then performed by the high-throughput platform of FIG. 1. Refer to FIGS. 27 and 29 for an understanding of how tis screen is performed. First, screening parameters are entered using a GUI tool such as that shown in FIG. 27. If limiting the time of the drug screen is the primary concern, the user enters a desired time per plate (typically in minutes) using the Time/Plate field of the GUI tool, and the estimated MSR and Cells/Well are calculated automatically and displayed. If the resulting MSR is deemed inappropriate, the user may choose to shorten or lengthen the Time/Plate as required to achieve the desired MSR. The MSR also depends on the number of cells per image which is also entered by the user using the Cells/Image field of the GUI tool. The actual MSR will be a function of the number of cells per image acquired as the drug screen is performed. If achieving a certain MSR is deemed more important, the user enters the desired MSR using the MSR field of the GUI tool and enters an average number of cells using the Cells/Image field. Then the Cells/Well value and estimated Time/Plate are calculated automatically and displayed in the corresponding fields of the GUI tool. In this case, the actual time will depend on the value in the Cells/Image field and the high throughput platform of FIG. 1 will acquire images until the desired MSR is achieved. The user can also enter the value in the Cells/Well field and the average number of Cells/Image and the MSR and Time/Plate will be calculated automatically and displayed in the corresponding fields.

The flow chart of FIG. 29 shows the steps executed by the high throughput platform of FIG. 1 in automated scanning. The drug screen may consist of scanning a single microtiter plate (with 96, 384 or any number of wells) or a stack of microtiter plates delivered by a plate robot for a multi-plate scan. The scan is initiated in step 2900 by the user after placing a plate on the microscope stage (or the plate is loaded by the robot). The platform then moves the plate to the first well (step 2910), performs autofocus (step 2920), acquires the color image in step 2930 (each color represents a different fluorescent dye staining a different cellular molecule and/or cellular compartment), performs image segmentation in step 2940 (finds the masks of the cellular compartments), separates compartments of overlapping cells using tessellation, also in step 2940, and measures FLIC in step 2950. In step 2960 a test is then performed to determine if enough cells have been measured to achieve the desired MSR or if the number of images has been acquired to achieve the desired time/plate. If not, in step 2970 the platform moves to the next field of view (image) within the same well and repeats the acquisition and analysis steps. When enough images have been analyzed, the platform moves the plate to the next well in step 2910 and repeats the same steps. When the last well in the experiment has been analyzed (step 2980), the plate is completed and either the next plate is automatically loaded (step 2990), or the scan is complete. When all of the plates in the experiment have been analyzed, the drug screen is finished.

System Design Considerations for Tessellation

An O(n log n) Voronoi Tessellation Algorithm: With reference to FIGS. 30a-30h, this section describes the algorithm used to create Voronoi tessellations for a collection of random points in the plane. The points come from an image analysis program that computes the position of various objects from a scanning cytometer. The objects may be cell nuclei or other images. The only important fact is that the objects can be represented by a set of nodes specified by X and Y coordinates. For cells, cell nuclei and other objects the assignee's U.S. Pat. Nos. 5,548,661 and 5,790,692, describe image segmentation techniques that can be used to locate the objects in the image. Once those or other image segmentation techniques have been used to create a mask of pixels describing the locations of the object pixels of each object, the centroids or other single-pixel node can be computed that represents the object for tessellation.

Figure 30A:
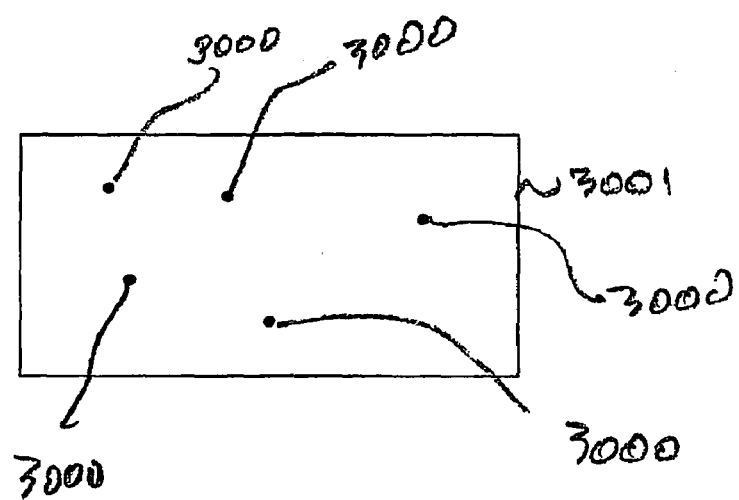
FIGS. 30a-30h are geometric figures including nodes, edges, circles, and polygons that illustrate various aspects of tessellation as used in this invention
Figure 30B:
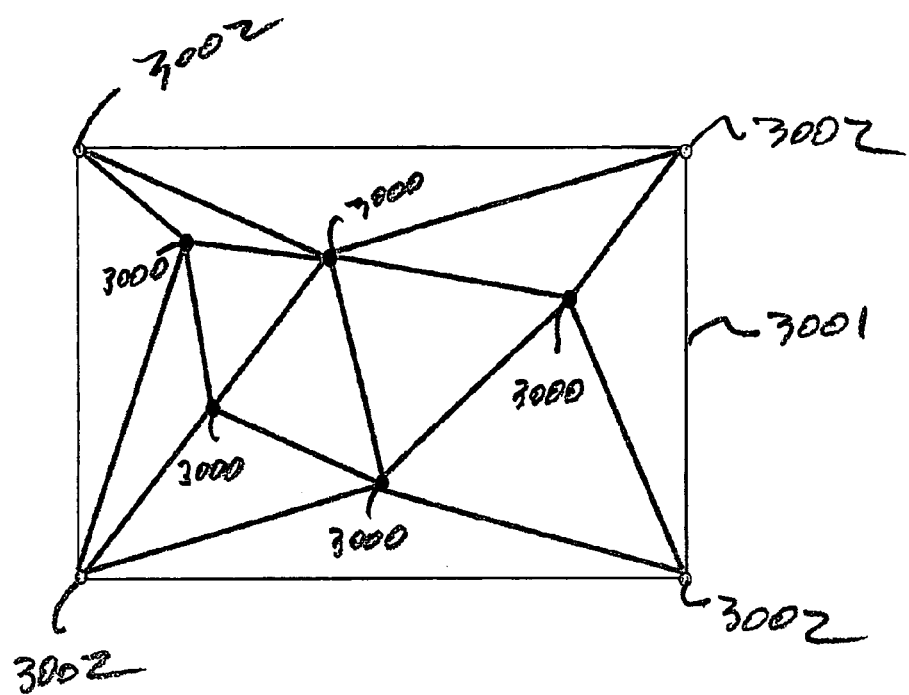

A useful objective is to tessellate a magnified, segmented image so that each node lies inside its own polygon. The interior of the polygon is closer to its node than to any other node. This tessellation is called the Voronoi tessellation, and it can be generated directly, or from its dual graph, a Delaunay triangulation of the plane, in which the nodes form the vertices of triangles. Refer to FIG. 30a, which shows a set of nodes 3000 in a plane 3001. In the tessellation algorithm employed in our invention, the four corners 3002 of the plane are added as additional nodes and the resulting set of nodes is triangulated, as shown in FIG. 30b.

Figure 30C:
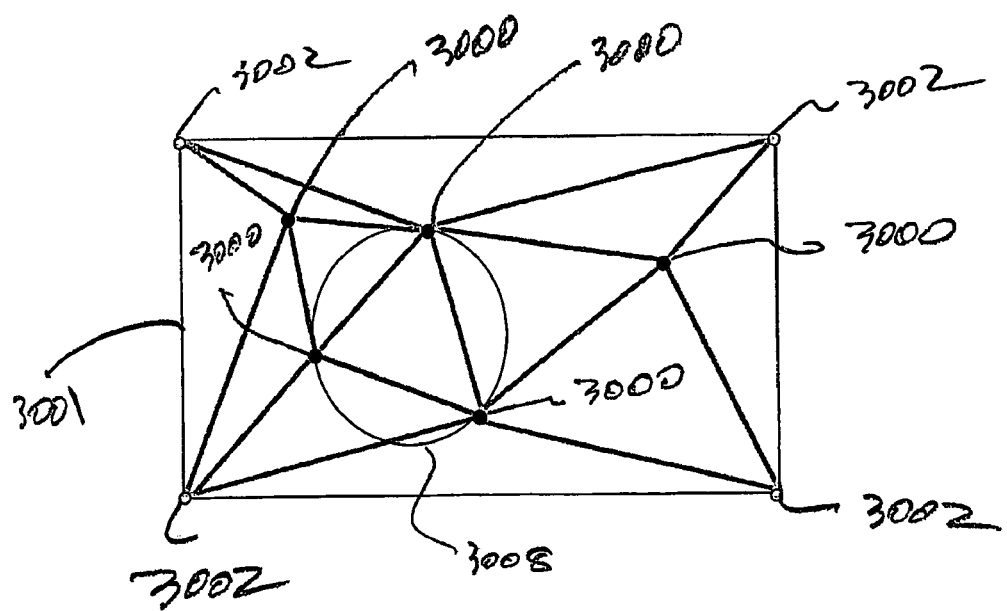

Many different triangulations are possible. The triangulation shown in FIG. 30c has the "Delaunay property," namely that the circle that circumscribes each triangle contains no nodes in its interior. In FIG. 30c, such a circle 3008 (called a "circumdisk") circumscribing the central triangle contains no other nodes. Each of the triangles has its own circumdisk, and no node lies in the interior of a circumdisk.

Figure 30D:
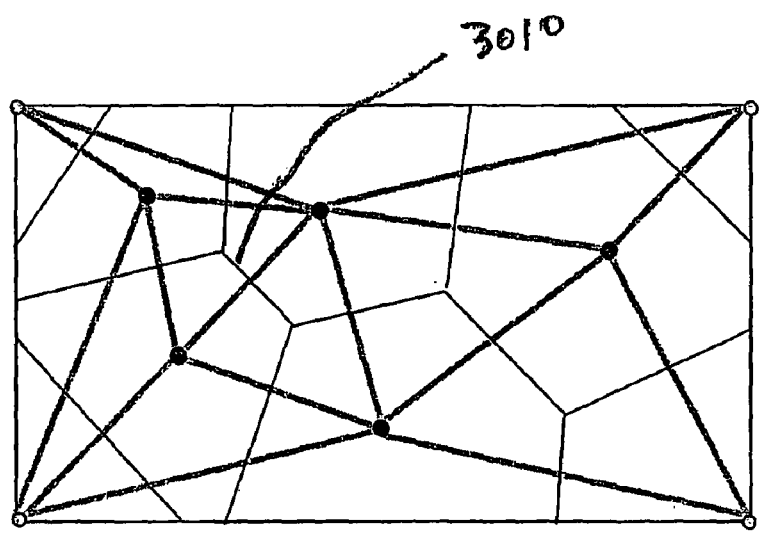

Note in FIG. 30c that each node is the vertex of several triangles, which can be ordered either clockwise or counterclockwise. By connecting the centers of the circumdisks of these triangles (for example, by line 3010), one obtains the "Voronoi tessellation," as shown in. FIG. 30d. A Voronoi tessellation is dual to the Delaunay triangulation. The polygon edges are perpendicular bisectors of the edges of the triangles. The region is now split up into polygons around each node. Each polygon contains all points closer to its node than to any other node. Note that the four corner nodes also have polygons assigned to them.

Ours is an efficient algorithm to create the Delaunay triangulation and Voronoi tessellation for an arbitrary collection of nodes in the plane. According to our algorithm, if n is the number of nodes, then our algorithm scales linearly with n in the memory requirements, and scales with n log n for time requirements. This is close to optimal. Using our algorithm, we have found that 100000 nodes can be triangulated and polygonized in under 5 seconds, with memory requirements on the order of 35 MB. A million nodes can be done in around 75 seconds, with 379 MB required for storage. The machine used is a Wintel box running at 800 MHz.

Presume computation of the Delaunay triangulation for a set of nodes. The minimal set of data needed for this is the following:

1) Node coordinates: An X and Y coordinate for each node, stored as floating point numbers. The most convenient way to do this is to assign each node an integer index, starting with 0 and going up to n-1, where n is the number of nodes. Then the X and Y coordinates are stored in two large double-precision arrays.

2) Triangle nodes: The indices of the three nodes that make up each triangle. The easiest way to store this data is by assigning each triangle an integer index, starting with 0 and going up to N-1, where N is the number of triangles. N is approximately 2n. Then one stores the nodes of each triangle in three integer arrays, in counterclockwise order going around the triangle.

It is also convenient (though not strictly necessary) to store the center coordinates and radius of the circumdisk of each triangle. These will be stored in double-precision arrays indexed by the triangle index. Given the coordinates of each of the three nodes of a triangle, it is a simple linear algebra problem to compute the coordinates of the center of the circumdisk Then the radius is given by the Euclidean distance from the center to any one of the nodes.

We next describe an algorithm for efficiently finding the coordinates for all the polygons in the diagram in one pass. The algorithm is as follows:

1) Create an array of lists of triangle indices, one list for each node. So the array of lists will be indexed by the node index.
2) For each triangle, get its three node indices. There is a list for each of these nodes. To each of these three lists, add the triangle index.
3) To construct the Voronoi polygon for any node, get its list of triangles. Order the list counterclockwise by computing the angle that the center of the circumdisk of each triangle makes with the node, and then sorting in increasing order. The centers of the circumdisks, ordered in this way, form the vertices of the Voronoi polygon for the node.

All of this can be implemented easily using Standard Template Library (STL) components. The coordinates and triangle nodes can be stored in vectors of doubles and integers. The array of lists can be implemented as a vector of vectors of integers. To minimize storage, the vectors should be sized in advance using the reserve( ) method of the vector class. For example, the coordinate arrays should have n entries reserved. The nodal arrays for triangles should have N entries reserved. The array of lists should have have n lists reserved, with each list having 8 entries reserved. It is rare for a node to have more than 8 triangles; in the few cases where a node has more than 8, the STL vector will automatically resize itself. This algorithm scales in time linearly with the number of nodes, and it executes much faster than the triangulation algorithm.

We now describe an iterative method for triangulating a set of nodes contained in some rectangle. At each stage, a valid Delaunay triangulation of k nodes will be assumed, and then the next node will be added and edges will be rearranged so as to yield a Delaunay triangulation of k+1 nodes.

Figure 30E:
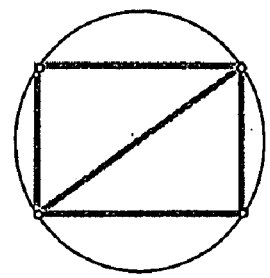

Initially, a Delaunay triangulation of the four corner nodes of the containing triangle is constructed. This is shown in FIG. 30e. With a Delaunay triangulation of the four corners of a rectangle, the same circle circumscribes both triangles, and its center is at the midpoint of the diagonal. Now presume successful triangulation a collection of k nodes, and that we want to add the next node. Assume that the new node lies in the interior of the existing triangulation. Since the description started with a bounding box, this is a safe assumption.

Figure 30F:
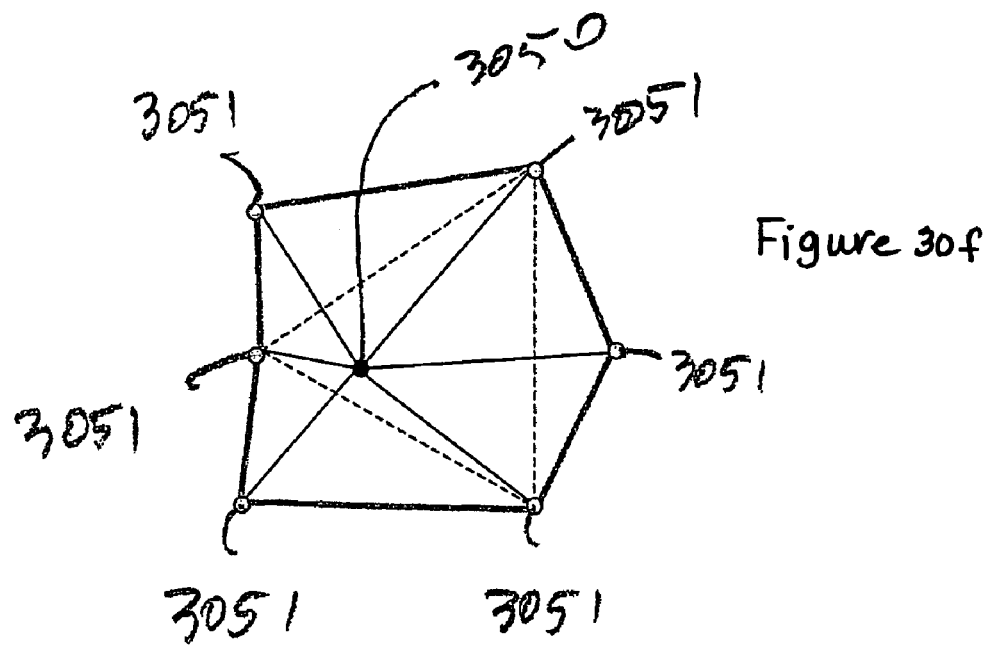

The algorithm for modifying the mesh is illustrated in FIG. 30f:

1) Find the set of all triangles whose circumdisks contain the new node. These triangles will have to be deleted, since a valid Delaunay triangulation never has a triangle whose circumdisks contain nodes.

2) The union of these triangles forms a polygon containing the new node. Delete all the triangle edges contained in the interior of this polygon.
3) Create new edges connecting the new node to each of the vertices of this polygon.

The node 3050 is the new node being inserted. It is contained in the circumdisks of four previously existing triangles, having a total of six nodes 3051. The six exterior edges connecting the nodes 3051 are left alone. The three interior edges shown by dashed lines are deleted. Six new edges (the black solid lines) are created, each connecting the new node 3050 to one of the outer nodes. By construction the circumdisk of each of the new triangles intersects the new node, and the new node is not in the interior of any other circumdisk. Hence, the new triangulation is still Delaunay. The operation has increased the total node count by one, the total triangle count by two, and the total edge count by three. This accounting holds true for each node added to the triangulation. Therefore, the final mesh will have approximately 2n triangles and 3n edges, where n is the number of nodes. Note that the initial mesh has 4 nodes, 2 triangles, and 5 edges. Accordingly, the exact result is that the mesh will have 2n-6 triangles and 3n-7 edges.

Thus far, we have described the algorithm above only generally. A complete description requires a specification of the data structures and the steps needed to carry out the steps. The simplest procedure is to use no new data structures. Step (1) can then be performed by a brute-force search of all triangles. Each triangle whose circumdisk contains the new node is added to a list. In practice, this list is small; it almost always contains fewer than 10 entries. Steps (2) and (3) can then be performed quickly. However, the brute-force search in step (1) requires an operation for each triangle, which is approximately twice the number of nodes. Since the brute-force approach requires a search for each node, the time to triangulate the mesh requires of order $n^2$ operations, and this is rather poor.

The algorithm thus far described is known as Watson's algorithm, and has been around since the 1970s. In the next section, we describe an improvement to this algorithm that substantially speeds up the triangulation process for large meshes.

The bottleneck in the triangulation scheme described above occurs where all circumdisks containing the new node to be inserted are found. If even one triangle whose circumdisk contains the new node can be found, then the search can be restricted to the nearest neighbors, which would substantially increase efficiency. So the problem reduces to finding that first triangle whose circumdisk contains the new node.

Our preferred solution is use of the so-called "sweepline" method. A sweepline algorithm for computing the Voronoi tessellation was published by S. Fortune in 1987. Our algorithm uses something similar for computing the Delaunay triangulation. The idea is to sort the nodes in increasing order of the X-coordinate. Ties would be broken by sorting on the Y-coordinate. Since we assume that all (x, y) pairs are distinct, this defines a unique ordering of the nodes to be inserted. We then insert nodes in this order, using the algorithm above, but now using an intelligent search rather than the brute-force search. One can imagine a vertical line sweeping across from left to right. At any time, the vertical line is located at the X-coordinate most recently inserted. All nodes to the left of the line have been inserted; all nodes to the right are not inserted yet.

A brute force sweepline algorithm searches backwards in the list of triangles. This list will have the most recently inserted triangles at the tail of the list. If the algorithm starts at the tail of the list, it will search the right-most triangles and will likely find one quickly whose circumdisk contains the next node to be inserted. This simple solution works well, and reduces the triangulation time to order n log n. But there is a faster search algorithm, which is also reasonably simple, so we'll describe that here.

Figure 30G:
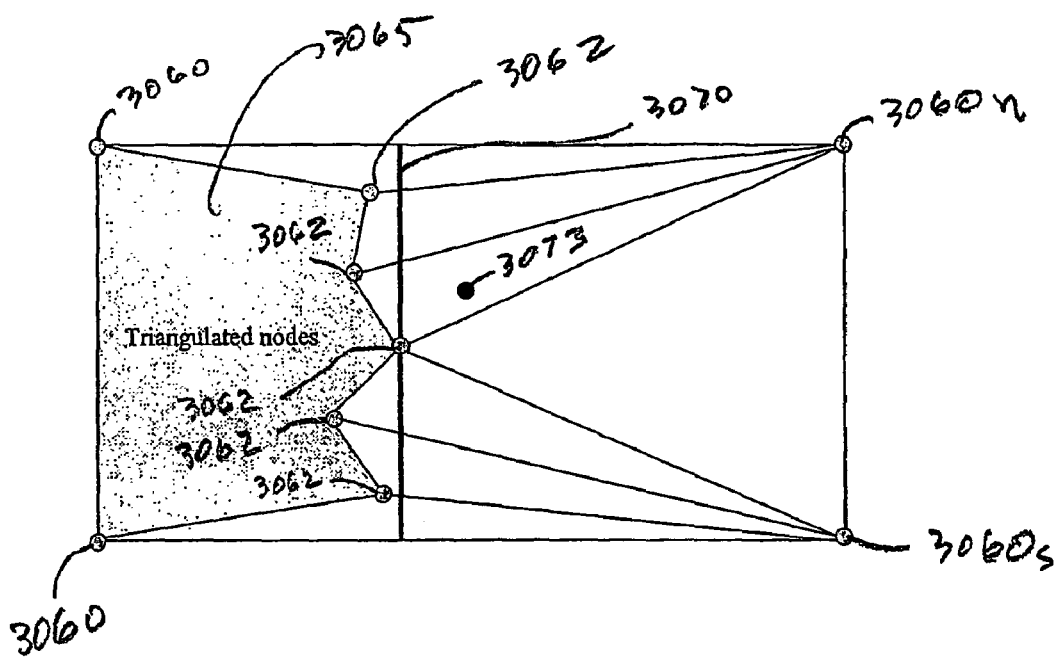

A faster search algorithm depends on the fact that nodes are inserted inside a rectangle that is triangulated to begin with. So the right side of the mesh consists of a large number of long, skinny triangles that contain one of the two corner nodes on the right, either the northeast or the southeast node. Our sweepline algorithm is illustrated in FIG. 30g. In this figure, the four corner nodes define the maximum extent of the region, and were triangulated first. The nodes 3062 in the interior of the rectangle have been inserted from left to right. The shaded region 3065 represents a large number (possibly millions) of nodes which have already been inserted. The vertical sweepline 3070 marks the line of demarcation. To its left, all nodes have been inserted into the mesh To its right, no nodes have been inserted. The red node is the next node in the list. Since it lies to the right of the sweepline, it must lie in one of the long skinny triangles containing either the northeast node 3060n or the southeast node 3060s (or it can lie in the large "central triangle" that contains both the northeast and southeast nodes). There are roughly sqrt(n) long skinny triangles connecting to the corner nodes. We put these into two lists, the "northeast list" and the "southeast list" and sort them by the slope of their lower edges. Then the node to be inserted will either be in the central triangle or it can be rapidly located in one of these lists using a binary search. The time to perform this search is of order log(sqrt(n)). It should be clear that the time to triangulate all the nodes is of order n log(sqrt(n)). Technically, this is still of order n log n, but it should be clear that the operation count is pretty small.

We have implemented this algorithm and its performance is of order n log n all the way up to half a million nodes, (which can be triangulated in less than 30 seconds). We see slightly more time required for a million nodes, but the reason is not clear. It could be memory allocation problems, or some other subtlety. We anticipate the need to do meshes with 100000 nodes as quickly as possible. The current implementation can create the mesh in under 5 seconds. We expect that this can be reduced by 10 to 20% by tweaking the code.

We now describe how to complete the list of triangles whose circumdisk contains the node to be inserted once the first triangle has been found using the algorithm given above. The solution to this requires bookkeeping. The idea is that all such triangles are adjacent. So as soon as the first one is found, one need only search all the nearest neighbors in some orderly way, until all of the possibilities have been eliminated. This is implemented as a recursive operation.

First, we create an STL set containing the indices of all triangles whose circumdisk contains the new node. We initialize it with the first triangle found, and then call a method that tests the triangle and recursively checks its three neighbors. The recursion stops if a triangle is already in the set, or if its circumdisk doesn't contain the node. We have found experimentally that these sets tend to be small and that it is actually faster to use an STL vector, to avoid the costs of insertion into a set. The effect is a speed boost of about 12%.

Figure 30H:
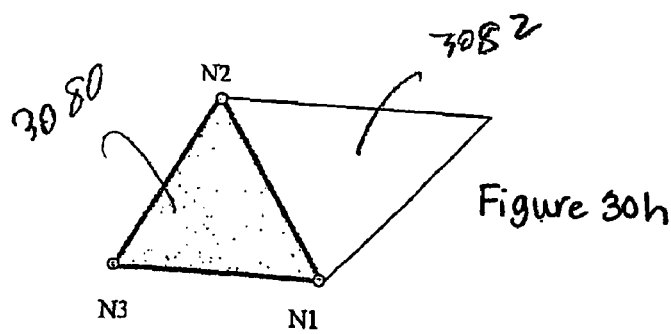

Next the neighboring triangles of each triangle must be found. The simplest way to do this is to maintain a map of each edge to the triangle on its right, as shown in FIG. 30h. In this figure, The three nodes of the shaded triangle 3080, $N_1$, $N_2$, and $N_3$ define three edges going counterclockwise around the triangle. The ordered pair ($N_1$, $N_2$) is mapped to the index of the triangle 3082 on their right. Likewise, the ordered pair (N$_2$,N$_1$) is mapped to the shaded triangle 3080.

The easiest way to do this mapping is to define an STL map that takes a pair of integers (the node indices) to a third integer (the index of the triangle to the right). However, for large meshes, the memory requirements are quite large. Furthermore, this is relatively slow. One should remember that there are a lot of edges. For each node in the mesh, there are approximately 6 directed edges.

An easier way to do the mapping is to make an STL vector of maps. The vector is indexed by nodes. The idea is that each node in the mesh points to several others (on average, 6 others). So each entry in the vector will be a map of an integer to an integer, mapping a node index to a triangle index. This is substantially more efficient than the map of integer pairs to integers.

However, even better results are obtainable. The map of an integer to an integer is still inefficient, since the main operations are inserting and deleting entries. It is faster and more space efficient to replace them by vectors of pairs of integers. The first entry in the pair is a node index; the second entry in the pair is the triangle index. So our data structure is a vector of vectors of pairs of integers. It is imperative to use the RESERVE method (a function in The MICROSOFT® VISUAL C++® programming environment to allocate a reasonable amount of space for the vectors. Otherwise, the STL will allocate several kB for each vector, and the memory requirements will be outlandish.

This is a common theme in working with the STL. Small sets (or small maps) are not as efficient as small vectors (or small vectors of pairs). Sets and maps are far more convenient to work with for the programmer, but they just can't match the efficiency of a vector when you're dealing with a handful of items. Ordinarily, this doesn't matter. But when one tries to optimize the inner loop, it can make sense to replace the set with a vector, as long as a small amount of space is reserved for the vector. The STL vector will grow automatically if necessary, but it's best to make this a rare event In our case, nodes typically average 6 neighboring nodes, with 8 neighbors being unusual, and more than 8 being rare.

The invention claimed is:

1. A method executable by an automated microscopy platform for measuring cell activity represented in an image of cells treated with an agent, the image obtained with the automated microscopy platform, comprising:
    segmenting cellular components in the image;
    separating segmented components of overlapping cells in the image; and
    determining, in the segmented, separated image, translocation of cellular material between first cellular compartments and second cellular compartments caused by the agent, by:
    measuring a first intensity of the cellular material in a first cellular compartment a of a cell;
    measuring a second intensity of the cellular material in a second cellular compartment b of the cell; and,
    determining fractional localized intensity $F_a$ of the cellular material in the first cellular compartment according to a ratio of the first intensity to a sum of at least the first and second intensities, according to:

$$F_a = \frac{\sum_{(x,y) \in a} I(x, y)}{\sum_{(x,y) \in a,b} I(x, y)}$$

where I(x, y), the emission intensity at a pixel location (x, y) in a cellular compartment, is determined according to:

$$I(x, y) = \int_0^z I_0 Q \varepsilon u \, dz$$

in which $I_0$ is an incident excitation intensity, Q is a quantum yield, $\varepsilon$ is an extinction coefficient, u is a local fluorophore concentration at pixel location (x, y), and z is the thickness of a column of cellular material at pixel location (x, y).

2. The method of claim 1, wherein segmenting includes enhancing contrast between the first cellular compartments and the background of the image, and between the second cellular compartments and the background of the image.

3. The method of claim 1, wherein separating includes tessellating the Image.

4. The method of claim 1, wherein:
    segmenting includes enhancing contrast between the first cellular compartments and the background of the image, and between the second cellular compartments and the background of the image; and,
    separating includes tessellating the image.

* * * * *